(12) United States Patent
Ashkenazi et al.

(10) Patent No.: US 11,000,357 B2
(45) Date of Patent: May 11, 2021

(54) DEVICE FOR FILTERING EMBOLIC MATERIAL IN A VASCULAR SYSTEM

(71) Applicant: Keystone Heart Ltd., Caesarea (IL)

(72) Inventors: Amit Ashkenazi, Haifa (IL); Tzeela Mikovski Shemesh, Ramat-Gan (IL); Valentin Ponomarenko, Haifa (IL)

(73) Assignee: Keystone Heart Ltd., Caesarea (IL)

( * ) Notice: Subject to any disclaimer, the term of this patent is extended or adjusted under 35 U.S.C. 154(b) by 0 days.

(21) Appl. No.: 15/760,203

(22) PCT Filed: Feb. 6, 2018

(86) PCT No.: PCT/EP2018/052953
§ 371 (c)(1),
(2) Date: Mar. 14, 2018

(87) PCT Pub. No.: WO2018/206160
PCT Pub. Date: Nov. 15, 2018

(65) Prior Publication Data
US 2019/0038392 A1 Feb. 7, 2019

(30) Foreign Application Priority Data
May 12, 2017 (EP) .................................. 17170949

(51) Int. Cl.
*A61F 2/01* (2006.01)
*A61B 18/00* (2006.01)
(52) U.S. Cl.
CPC ................ *A61F 2/013* (2013.01); *A61F 2/01* (2013.01); *A61B 2018/00351* (2013.01); *A61F 2002/016* (2013.01); *A61F 2230/0006* (2013.01)

(58) Field of Classification Search
CPC .............. A61F 2/013; A61F 2230/0006; A61F 2002/016; A61F 2018/00351; A61F 2/01
(Continued)

(56) References Cited

U.S. PATENT DOCUMENTS 8,974,490 B2 * 3/2015 Jonsson .................... A61F 2/01
606/200
2010/0179647 A1 7/2010 Carpenter et al.
(Continued)

FOREIGN PATENT DOCUMENTS

EP 2732794 A1 5/2014
EP 2859864 A1 4/2015
(Continued)

OTHER PUBLICATIONS

WIPO, European International Search Authority, International Search Report and Written Opinion dated Mar. 1, 2018 in International Patent Application No. PCT/EP2018/052953, 10 pages.
(Continued)

*Primary Examiner* — George J Ulsh
*Assistant Examiner* — Andrew P. Restaino
(74) *Attorney, Agent, or Firm* — Inskeep IP Group, Inc.

(57) ABSTRACT

An embolic protection device for transvascular delivery to an aortic arch of a patient for protection of side branch vessels of said aortic arch from embolic material. The device comprises a support frame, wherein at least a distal or a proximal portion of the support frame is a spring section configured for providing a radial force between the support frame and a wall of the aortic arch when in an expanded state.

16 Claims, 17 Drawing Sheets

(58) Field of Classification Search
USPC .......................................................... 606/200
See application file for complete search history.

(56) References Cited

U.S. PATENT DOCUMENTS

| | | |
|---|---|---|
| 2013/0123835 A1 | 5/2013 | Anderson et al. |
| 2013/0218194 A1* | 8/2013 | Jonsson ................. A61F 2/013 606/200 |
| 2014/0172006 A1* | 6/2014 | Stack ..................... A61F 2/013 606/200 |
| 2016/0175084 A1* | 6/2016 | Johnson ................. A61F 2/013 606/200 |
| 2016/0302909 A1* | 10/2016 | Kelly ..................... A61F 2/013 |
| 2016/0310255 A1 | 10/2016 | Purcell et al. |
| 2017/0189160 A1* | 7/2017 | Krahbichler ..... A61B 17/12172 |

FOREIGN PATENT DOCUMENTS

| | | | |
|---|---|---|---|
| JP | 2009273926 A | 11/2009 | |
| JP | 2014522264 A | 4/2014 | |
| JP | 2017501840 A | 1/2017 | |
| WO | WO 99/05992 A1 | 2/1999 | |
| WO | WO2010/026240 A1 | 3/2010 | |
| WO | WO 2012/158590 A1 | 11/2012 | |
| WO | WO2015/104645 A2 | 7/2015 | |
| WO | WO 2015/104645 A2 | 7/2015 | |
| WO | WO2015/177322 A1 | 11/2015 | |

OTHER PUBLICATIONS

Japan Patent Office, Examination Report dated Sep. 29, 2020 in Japanese Patent Application No. 2018-566543, 9 pages.

\* cited by examiner

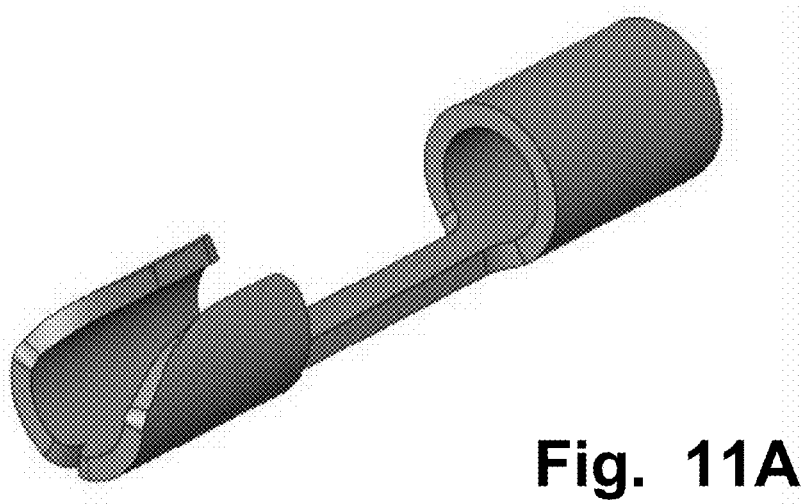
Fig. 11A
40
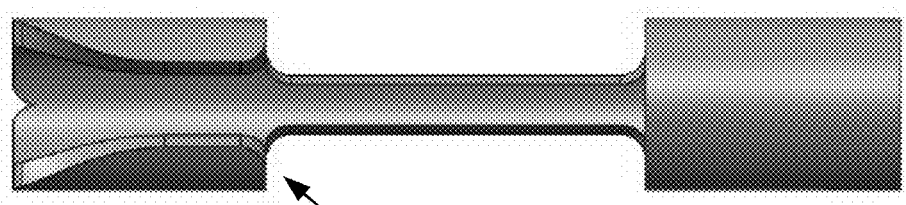
40 Fig. 11B

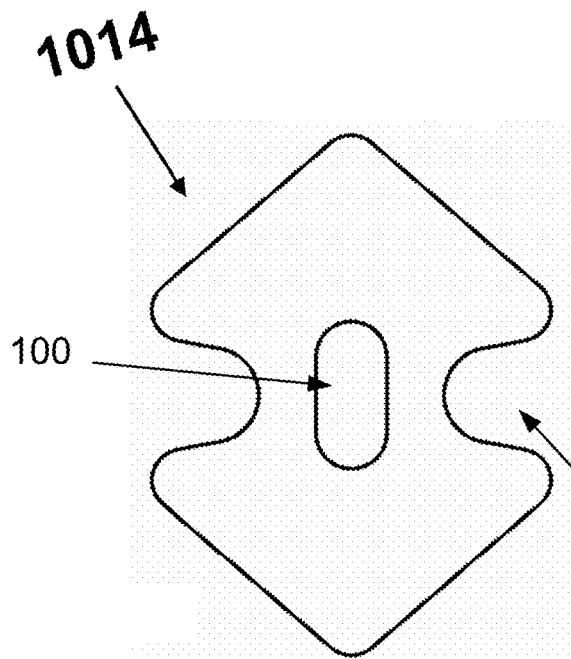
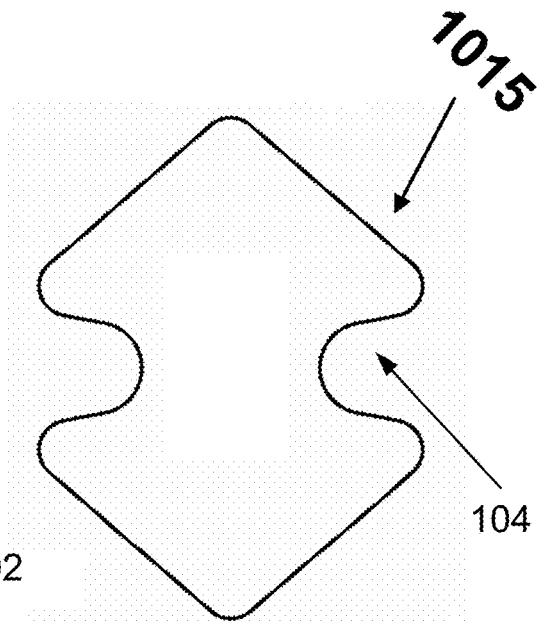
Fig. 14A
Fig. 14B
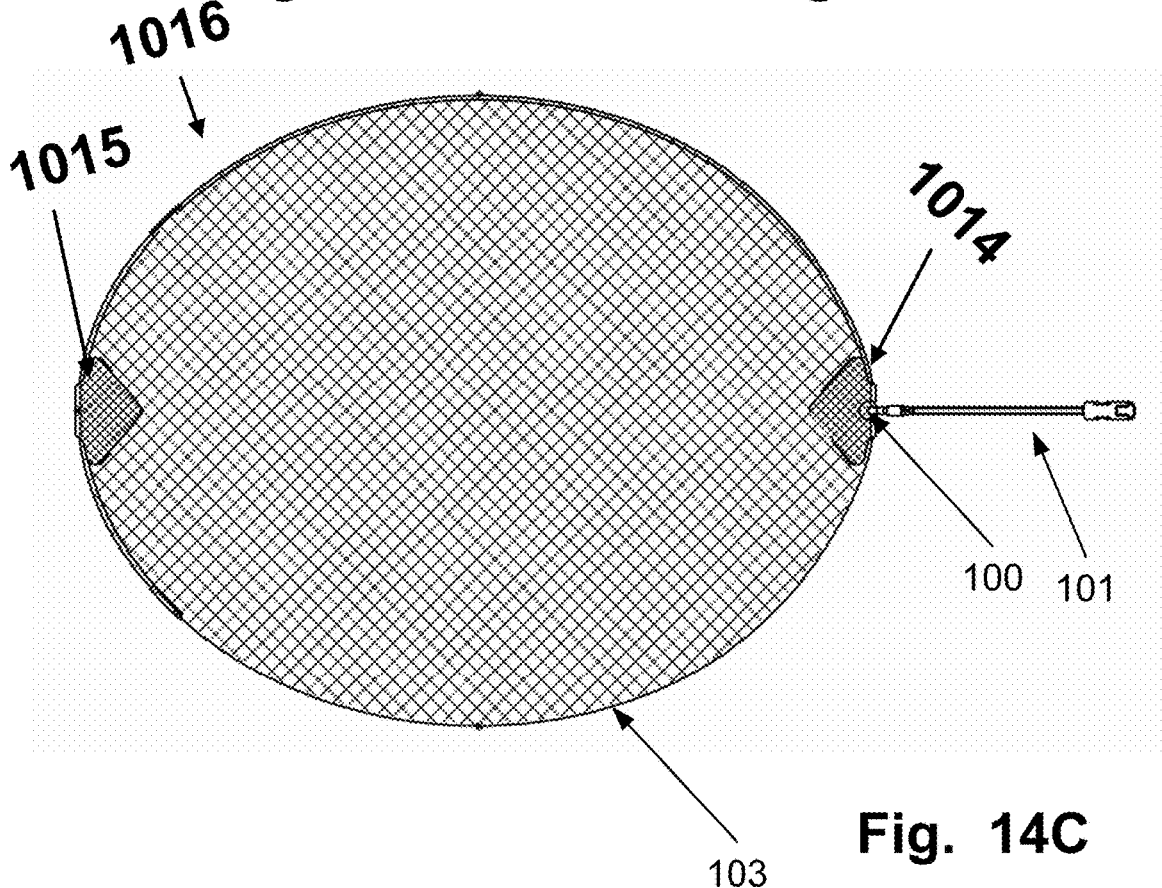
Fig. 14C

DEVICE FOR FILTERING EMBOLIC MATERIAL IN A VASCULAR SYSTEM

RELATED APPLICATIONS

This application is the U.S. National Phase of and claims priority to International Patent Application No. PCT/EP2018/052953, International Filing Date Feb. 6, 2018, entitled A Device For Filtering Embolic Material In A Vascular System; which claims benefit of European Application No. 17170949.6 filed May 12, 2017; both of which are incorporated herein by reference in their entireties.

BACKGROUND OF THE INVENTION

Field of the Invention

This disclosure pertains in general to intra-aortic devices and methods to prevent emboli from entering arteries branching from the aorta, e.g., arteries that lead to the brain.

Background of the Disclosure

Particles such as emboli may form, for example, as a result of the presence of particulate matter in the bloodstream. Particulate matter may originate from for example a blood clot occurring in the heart. The particulate may be a foreign body, but may also be derived from body tissues. For example, atherosclerosis, or hardening of the blood vessels from fatty and calcified deposits, may cause particulate emboli to form. Moreover, clots can form on the luminal surface of the atheroma, as platelets, fibrin, red blood cells and activated clotting factors may adhere to the surface of blood vessels to form a clot.

Blood clots or thrombi may also form in the veins of subjects who are immobilized, particularly in the legs of bedridden or other immobilized patients. These clots may then travel in the bloodstream, potentially to the arteries of the lungs, leading to a common, often-deadly disease called pulmonary embolus. Thrombus formation, and subsequent movement to form an embolus, may occur in the heart or other parts of the arterial system, causing acute reduction of blood supply and hence ischemia. The ischemia damage often leads to tissue necrosis of organs such as the kidneys, retina, bowel, heart, limbs, brain or other organs, or even death.

Since emboli are typically particulate in nature, various types of filters have been proposed in an attempt to remove or divert such particles from the bloodstream before they can cause damage to bodily tissues.

Various medical procedures may perturb blood vessels or surrounding tissues. When this occurs, potentially harmful particulates, such as emboli, may be released into the blood stream. These particulates can be damaging, e.g., if they restrict blood flow to the brain. Devices to block or divert particulates from flowing into particular regions of the vasculature have been proposed but may not eliminate the risks associated with the release of potentially harmful particulates into the blood stream during or after particular medical procedures.

Improved devices for blocking or diverting vascular particulates are under development, but each intravascular procedure presents unique risks.

As intravascular devices and procedures, such as transcatheter aortic valve implantation (TAVI), become more advanced, there is an emerging need for features that provide these devices with improved ease of use, intravascular stability, and embolic protection.

Possible areas of improvements of such devices and procedures include "windsailing" of devices with pulsatile blood flow, leakage of fluid and/or particulate matter at peripheral portions of devices during use thereof, secure positioning in a patient during use and/or retrievability, etc.

Hence, an improved intravascular device, system and/or method would be advantageous and in particular allowing for increased flexibility, cost-effectiveness, and/or patient safety would be advantageous.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a device, system or method according to the appended patent claims for providing a collapsible embolic protection device for transvascular delivery to an aortic arch of a patient, for protection of side branch vessels of the aortic arch from embolic material.

In some aspects of the disclosure, an embolic protection device for transvascular delivery to an aortic arch of a patient for protection of side branch vessels of the aortic arch from embolic material is described. The device includes a support frame, wherein at least a distal or a proximal portion of the support frame may be a spring section configured for providing a radial force between the support frame and a wall of the aortic arch when in an expanded state. The device may further include a filter member attached to the support frame, and configured for preventing the embolic material from passage with a blood flow into the side branch vessels of the aortic arch.

Further examples of the embolic protection device are disclosed in accordance with the description and the dependent claims.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which the schematic illustrations of FIGS. 1A and 1B are illustrating an example of an embolic protection device for transvascular delivery;

FIGS. 11A to 11B are illustrating an example of a stopper member;

FIGS. 14A to 14C are illustrating an example of stickers or patches that may be used at a distal and/or a proximal end of the embolic protection device.

DESCRIPTION OF EXAMPLES

The following disclosure focuses on examples of the present disclosure applicable to an embolic protection device, such as a collapsible embolic protection device, for transvascular delivery to an aortic arch of a patient for protection of side branch vessels of the aortic arch from embolic material.

Figure 1A:
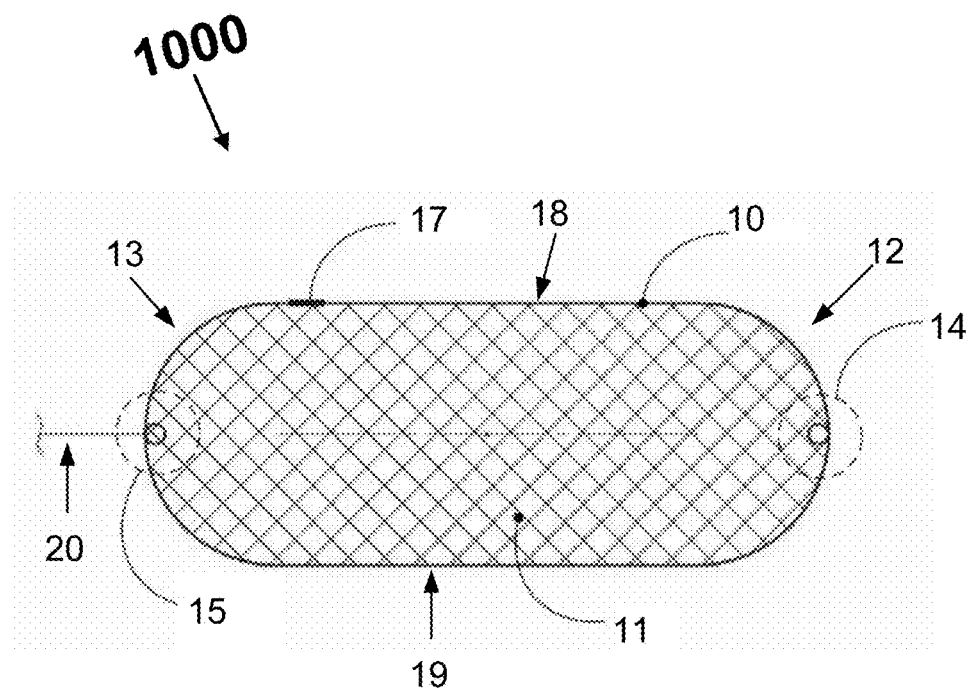
Figure 4:
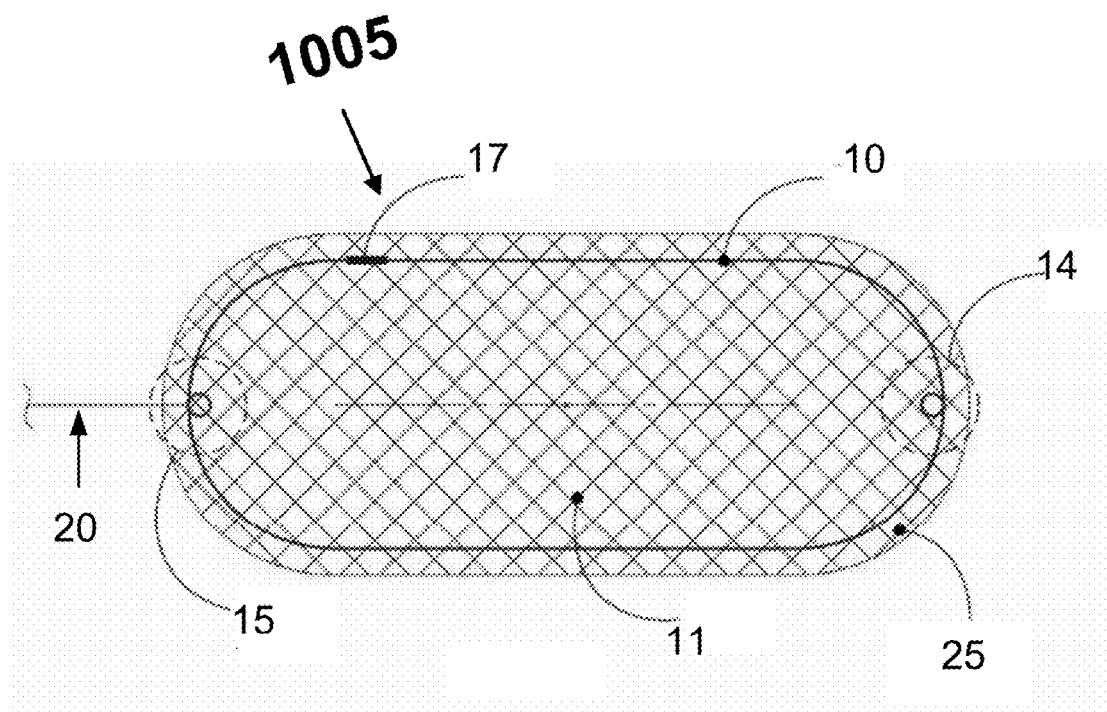
FIG. 4 is illustrating an example of an embolic protection device for transvascular delivery with an extended or enlarged filter member.

FIG. 1A is illustrating an embolic protection device 1000. The embolic protection device is collapsible, such as crimpable, to be arranged in a transvascular delivery unit. The protection device 1000 includes a support frame 10 and a filter member 11 attached to the support frame 10. The support frame may be, in some examples, a complete hoop completely surrounding a periphery of the filter member 11. In some examples, the filter member 11 may extend (partly or entirely) outside the periphery defined by support fame 10, and thereby create a collar or rim, as illustrated in FIG. 4. The collar or rim may improve apposition with the vessel wall rough texture. In some examples, the collar or rim may be made from a different material than the filter member 11.

The protection device 1000 may further include a connection point either at the support frame 10 or at the filter member 11. The connection point is used for connecting the embolic protection device 1000 to a transvascular delivery unit. Preferably the connection point is arranged off-centre at a proximal portion of the embolic protection device 1000. In some examples, a connection point may be arranged on a stem at distance from the filter membrane 11 and the support frame 10.

Figure 1B:
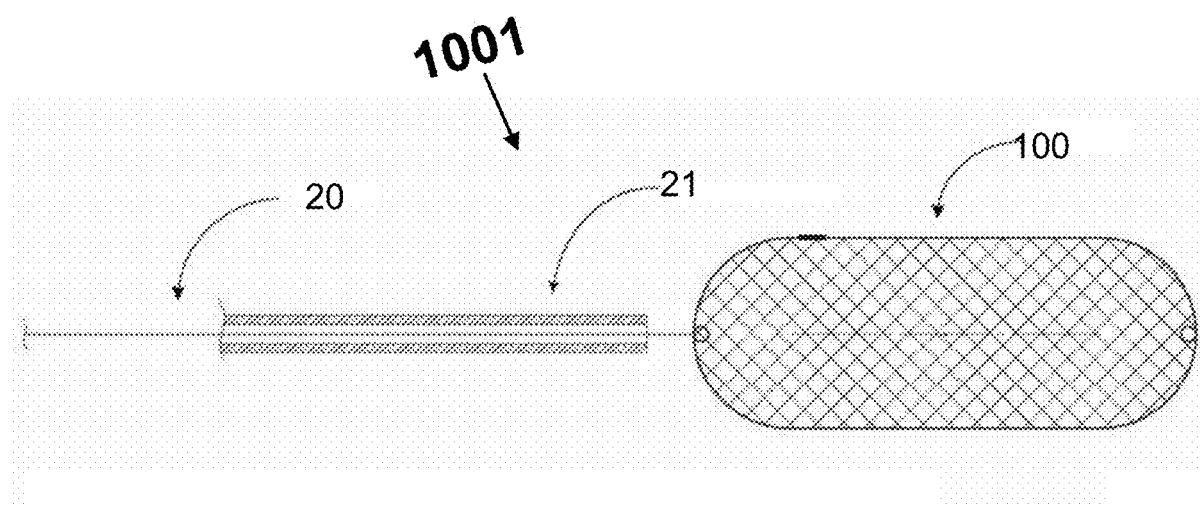

For positioning a protection device 1000 in an aorta, the device 1000 of the disclosure may be attached to and delivered by a transvascular delivery unit, for example as illustrated in FIG. 1B. The transvascular delivery unit may be, for example, a catheter or sheath, and the protection device 1001 may be attached to the transvascular delivery unit according to methods known in the art, or by a connector mechanism 20. In some examples, the transvascular delivery unit may comprise a connector mechanism 20, such as a wire, rod or tube, for example, a tether, a delivery wire, or a push wire etc. The connector mechanism 20 may be connected to the connection point. In some examples, the connector mechanism 20 may be permanently connected to the embolic protection device 1001. Thereby the embolic protection device 1001 may be delivered and withdrawn using the same connector mechanism 20. Further, the connector mechanism 20 may be used to hold the embolic protection device 1001 in place during a medical procedure.

In some examples, the connector mechanism 20 may be detachably connected to the embolic protection device 1001.

The distal end and/or the proximal end of the support frame 10 may be made from a spring section 12, 13. Each spring section 12, 13 is a pre-loaded spring that function as an engine and is configured for quickly expand or open-up a collapsed or crimped embolic protection device 1000 from a collapsed state to an expanded state and for providing a radial force between the support frame 10 and a wall of the aortic arch, when the support frame 10 is in an expanded state. The spring sections 22, 23 are engines being pre-shaped open springs. The spring sections 22, 23 may have a radius wider than the embolic protection device. Different radius of the opening may provide different forces.

The spring sections may provide improved apposition with aortic arch walls which may improve fixation of the device 1000 and the sealing between the device and the wall of the aorta, which may reduce paraframe leakage. The force from the spring sections may also avoid distortion of the support frame 10 when a radial force is applied. The force from the spring sections 12, 13 also tends to position the embolic protection device 1000 at about mid-vessel diameter, as illustrated for example in FIGS. 12A to 12C. Hence provides an embolic protection device with improved self-positioning and alignment properties.

The force provided by the spring sections 12, 13 may also reduce windsailing, in most cases to none.

The spring sections 12, 13 are preferably heat treated to form the spring sections and to provide spring properties. The spring sections are in some examples, formed as open springs and are wider than the protection device before the device is assembled.

By arranging a spring section 13 proximally, there will be an improved coverage of the landing zone. The landing zone is the area every guidewire will hit the aortic arch, see reference 80 in FIG. 12C. An improved coverage and sealing of the landing zone may help to prevent the passage of devices over (along) the protection device 1000 (through the aortic arch), for example by leading a guide wire below the protection device 1000.

Each spring section 12, 13 has a bend shape, such as a shallow U-shape, or is curved. In examples where the support frame 10 only has one spring section 12, 13 at either the distal or the proximal end, the rest of the support frame 10 has a deeper U-shaped form. This deeper U-shaped form does not have the same springy properties as the spring section 12, 13. In examples where the support frame 10 has a spring section 12, 13 at both the distal and the proximal ends, the support frame may have straight central sections 18, 19 formed between spring sections 12, 13. When using straight central sections 18, 19, these are substantially straight before the device is assembled. After the device is assembled, the straight central sections 18, 19 may bulge or obtain a curvature due to forces in the support frame from the spring sections, compare e.g. FIG. 2B.

In some examples, the support frame 10 may be made of two parts, wherein the first part may be a distal spring section 12 which may be pre-shaped to a shallow U-shape. The second part may be the proximal spring section 13 and the side sections 18, 19, which may be pre-shaped to a deeper U-shape than the first part.

Alternatively, and/or additionally, in some examples, the support frame 10 may be made of two parts, wherein the first part may be a distal spring section 12 which may be pre-shaped to a shallow U-shape. The second part may be the proximal spring section 13 and the side sections 18, 19 which may be a straight wire (apart from a possible spring element) which get shaped into a deeper U-shape when attached to the distal spring section 12.

Alternatively, the support frame 10 may be made of two parts, wherein the first part may be a proximal spring section 13 which may have a shallow U-shape. The second part may be the distal spring section 12 and the side sections 18, 19 which may be shaped to a deeper U-shape than the first part. In some examples, the straight central sections may function as spring engines in a longitudinal direction of the embolic protection device.

Additionally, and/or alternatively, in some examples, the spring sections 12, 13 are heat treated to form the spring sections, while the rest of the support frame 10 is not heat treated. This will give the support frame 10 a flexibility that may further improve apposition of the embolic protection device 1000 with the aortic arch walls as it complies better with the rough texture of the vessel wall.

Further, by heat treating all sections there may be forces at the transitions between the segments, such as at joints between segments, applicable to the wall of the aortic arch. Also, if the wire is made from a single wire being heat treated, there will be fewer connectors for joining the different sections, which may also improve the forces from the transitions between the segments to the wall of the aortic arch.

An advantage of only heat treating the spring sections 12, 13, and not the other sections, is that the forces from the spring sections will be comparatively stronger.

To further improve the force, some segments may be made thicker than others, for example, at the distal end of the support frame 10, the distal spring section 12 may be thicker than the rest of the support frame, and weaker proximally. This may also make it easier to crimp the support frame 10, e.g. into a catheter lumen for delivery, or for improved exiting such lumen when deploying the embolic protection device.

Alternatively, in some examples, both the distal and the proximal spring sections are made thicker than the rest of the support frame. This will improve the spring forces at both the proximal and the distal end. The thicker spring sections may open up the support frame while the thinner sections are more compliant with the vessel wall.

Alternatively, in some examples, the distal spring section 12 may be made thicker than the proximal spring section 13. Additionally, in some examples, the middle sections 18, 19, may be made of the same thickness as the proximal section 13. In some other examples, are the middle sections 18, 19, made of the same thickness as the distal section 12.

Alternatively, in some examples, both the spring sections and the central sections are made thicker than the joints or transition segment(s) between the thicker sections that may be made thinner. This will provide strong forces on all sides while avoiding the issues of making the whole support frame rigid. Making the whole support frame rigid may force the spring sections to close and not efficiently cover tortuous anatomies with the embolic protection device.

By utilizing different thicknesses or cross sections of different sections, a support frame may be obtained having a configuration with different forces at different segments. Additionally, and or alternatively, the at least distal or proximal spring section 12, 13 may include a spring element 14, 15. The spring element 14, 15 may in some examples be a loop or helix, a small spring or any other type of spring arranged at about the centre of each of the distal or proximal spring section 12, 13. The spring element, 14, 15 is used for increasing the force applied by the support frame 10 on the walls of the aortic arch.

As previously described, the spring sections 12, 13 are used for applying a force by the support frame 10 on the wall of aortic arch which may improve the sealing effect between the collapsible embolic protection device and the wall of the aortic arch, as well as provide an improved self-stabilizing effect. Additionally, the use of spring sections 12, 13 may improve the positioning and self-alignment of the device in the aortic arch.

Additionally and/or alternatively, in some examples, the connector mechanism 20 may be attached to the support frame 10 allowing the protection device to pivot axially but not radially at the joint between the support frame and the connector mechanism 20, for example by attaching the connector element via the proximal loop 15.

The spring element, especially the proximal spring element 14, may in some examples function as a crimp element to improve the collapsibility of the embolic protection device by elongating the device longitudinally. Thereby allows to embolic protection device 1000 to be crimped into a sheath with small diameter.

Spring elements 14, 15 may in some examples, for example when the spring elements 14, 15 are loops, be formed to either protruding outwards (relative the periphery/footprint defined by the support frame) or formed to be protruding inwards (relative the periphery/footprint defined by the support frame) as illustrated in FIG. 1A. Arranging or forming one or more of the spring elements 14, 15 to protrude inwards improves attachment of the filter member 11 to the support frame 10. Also, having one or more of the spring elements 14, 15 arranged to protrude inwards improves the contact between the support frame 10 and the walls of the aortic arch as there is nothing protruding or extending further than the support frame 10 (smooth apposition to the aortic wall vessel tissue, further improvable by a collar mentioned herein).

The support frame 10 may be made from a wire, such as a spring wire, or being laser cut from a tube, ribbon, sheet, or flat wire, etc. The support frame 10 may be of a single wire. In some examples, the support frame 10 is made from a twisted single wire. Alternatively, in some examples the support frame 10 may be made of at least two wires being twisted, braided or knitted.

The support frame 10 may be in some examples made from joint free ring. In other examples the support frame 10 made be formed from a ring having at least one joint 17. A joint 17 may be for example a fixation like a soldering, welding, or a clamp.

The support frame 10 may be shaped into an elongated shape, substantially elliptical, oblong, oval, or cone slot shaped. Alternatively, other shapes may be used, such as circular or rectangular. Because the aortic anatomy can vary between individuals, examples of the intra-aortic device of the disclosure may be shaped to adapt to a variety of aortic anatomies.

Figure 2A:
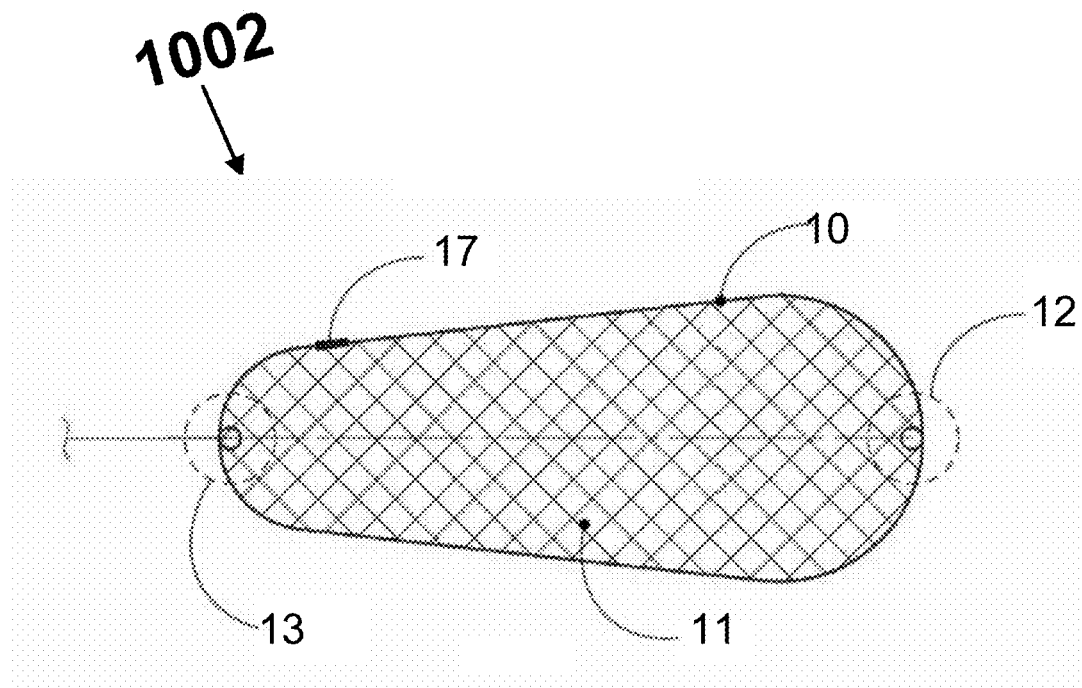
FIGS. 2A and 2B are illustrating an example of an embolic protection device for transvascular delivery.
Figure 2B:
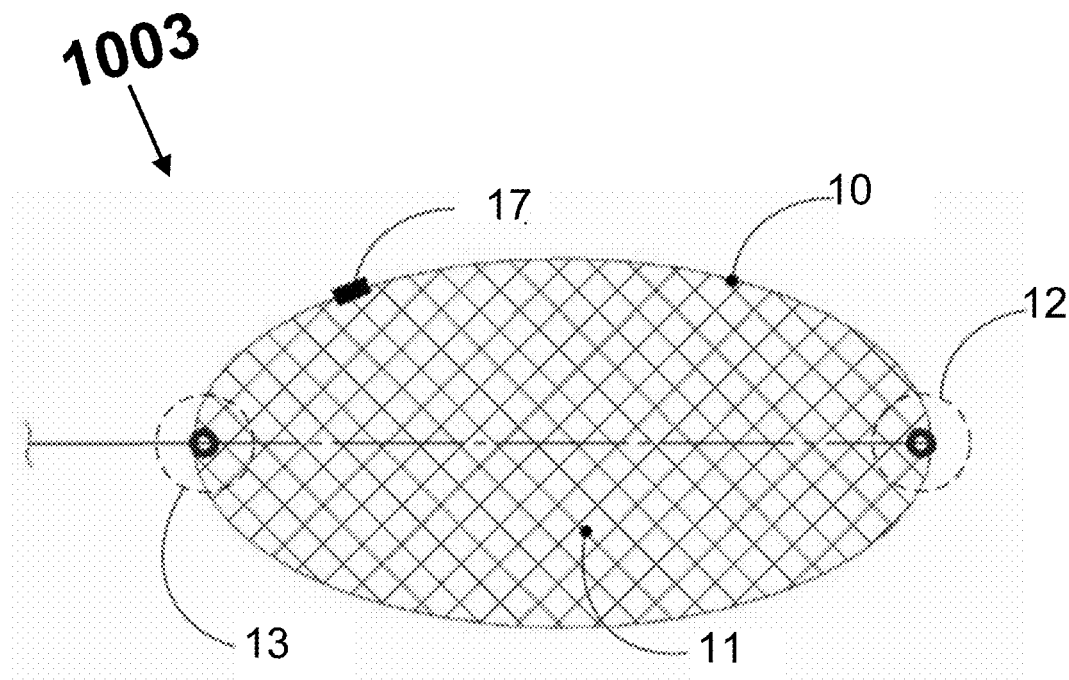

An example of an elongated or oblong shaped support frame 10 may be a slot shaped support frame 10 as illustrated in FIG. 1A. A collapsible embolic protection device 1002 having a cone slot shaped support frame 10 is illustrated in FIG. 2A. A collapsible embolic protection device 1003 having an elliptic shaped support frame 10 is illustrated in FIG. 2B.

The size of the collapsible device may be pre-sized and pre-formed to accommodate various patient groups (e.g., children and adults) or a particular aortic anatomy. The support frame 10 may be, in some examples, substantially planar. In some examples, the support frame 10 may have a width greater than the diameter of the aortic arch into which it is configure to be positioned in use, such as about 50% greater than the diameter of the aortic arch, such as 50% greater than the cross-sectional chord of an aorta of a subject, in which the collapsible embolic protection device 1000 may be placed. Additionally, in some examples, a support frame 10 may be longer than the aortic arch opening, such as about 20% longer than the arch opening, such as 20% longer than an approximate distance between an upper wall of an ascending aorta of a subject, distal to an opening of an innominate artery, and an upper wall of a descending aorta of a subject, proximal to an opening of a left subclavian artery.

By making the support frame 10 wider than the diameter of the arch, such as about 50% wider, and longer than the aortic arch opening, such as about 20% longer, as defined above, the self-positioning of the device positioning about mid vessel diameter may be improved and thus improve the apposition with aortic arch walls. This will make it easier to deploy the embolic protection device and improve the sealing against the walls. It may also improve the coverage of all three side vessels, innominate (brachiocephalic) artery, left common carotid artery, or left subclavian artery) which are supplying blood to the brain.

The support frame 10 may be fabricated in whole or in part from, e.g., nitinol or metal, superelastic or shape memory alloy material, readily malleable material, or polymer, e.g., nylon. The metal may include, e.g., tantalum or platinum.

The filter member 11 prevents particles (e.g., emboli) typically having a dimension between about 50 μm and about 5 mm (e.g., 50 μm, 100 μm, 200 μm, 300 μm, 400 μm, 500 μm, 750 μm, 1 mm, 2 mm, 3 mm, 4 mm, or 5 mm) in an aorta from passing into blood vessels (e.g., innominate (brachiocephalic) artery, left common carotid artery, or left subclavian artery) supplying blood to the brain. Accordingly, one or more lateral dimensions of the pores of the filter can be between about 50 μm and about 5 mm (e.g., 50 μm, 100 μm, 200 μm, 300 μm, 400 μm, 500 μm, 750 μm, 1 mm, 2 mm, 3 mm, 4 mm, or 5 mm). The filter may be, e.g., a mesh made from a plurality of fibers made of polymer, nylon, nitinol, or metal, or a combination thereof. The mesh may be made from woven fibers. Fibers may be from about 20 to 50 μm in thickness. Alternatively, the filter may be a perforated film. When a perforated film is present, the pores formed in the perforated film may include pores of varied or unvaried shape (e.g., rectilinear or rhomboid pores), have a varied or constant density across the film, and/or have a constant or varied size. The size of the pores of the filter allows passage of blood cells (e.g., red blood cells (erythrocytes), white blood cells (leukocytes), and/or platelets (thrombocytes)) and plasma, while being impermeable to particles (e.g., emboli) larger than the pore dimensions. Emboli filtered by the mesh of the filter of the present disclosure are typically particles larger in one or more dimensions than an aperture of the mesh of the filter.

In some embodiments, a filter member or mesh may be configured from woven fibers and is affixed to a support frame so that its yarn orientation is at angles that are not right angles to the support frame. For example, in some embodiments, the mesh may be affixed to the support frame so that the weave (warp and weft) of the mesh or weave may be at for example 45° angles from a base or lateral portion of the support frame. In some examples, the weave (warp and weft) of mesh may be at for example 30-60°, such as 35-55°, angles from a base or lateral portion of the support frame. When set at a non-right angle to the support frame, the mesh may stretch, expand or contract with greater flexibility than when such weave is at right angles to the support frame. Collapsibility or crimpability of the embolic protection device is advantageously improved in this manner.

Various catheters or sheath may be used as part of the present disclosure. Any catheter or sheath known in the art to be configured for guiding medical instruments through vasculature may be used (e.g., stent installation catheter, ablation catheter, or those used for transcatheter aortic valve implantation (TAVI) or percutaneous aortic valve replacement (PAVR) procedures, e.g., as described in U.S. Pat. No. 5,026,366). Additionally or alternatively, the device may include a pigtail catheter, which may be of size 6F or smaller (e.g., 1F, 2F, 3F, 4F, 5F, or 6F) and include a radiopaque material to facilitate tracking the progress of various elements of the device. Other catheters that can be used as part of the disclosure include any catheter used in procedures associated with a risk of embolism, which would benefit by including an intravascular filter as part of the procedure.

The filter member 11 may be substantially flat or dome shaped. The dome shape of the filter member 11 may be in some examples about the size of the support frame 10. Alternatively, in some examples, the filter member 11 may be dome shaped at either the distal or proximal end. A dome shaped filter membrane 11 may improve the space underneath the embolic protection device 1000. It may also improve the filtering due to a larger filter area.

A device of the disclosure may incorporate radiopaque elements. Such radiopaque elements can be affixed to, or incorporated into the device. For example, portions of the frame, filter, or catheter may be constructed of OFT wire. Such wire can contain, e.g., a core of tantalum and/or platinum and an outer material of, e.g., nitinol.

FIG. 1B is illustrating a system 1001 of a collapsible embolic protection device 100 in accordance to the description, such as illustrated in FIG. 1A. The embolic protection device 100 is connected to a transvascular delivery unit. The transvascular delivery unit is here illustrated with a connection mechanism 20 being a wire or tether. The connection mechanism 20 may be made from a biocompatible metal and is attached to the support frame of the embolic protection device 100. The frame connection mechanism 20 is here illustrated as connected directly to the spring element of the support frame. The attachment may be made by a loop, latch or with a clamp. The attachment should be strong and flexible enough to push the device out of the sheath. FIG. 1B further illustrates a tube or sheath 21 used for delivering the embolic protection device 100 used for delivering the embolic protection device 100 to the working zone.

Figure 3A:
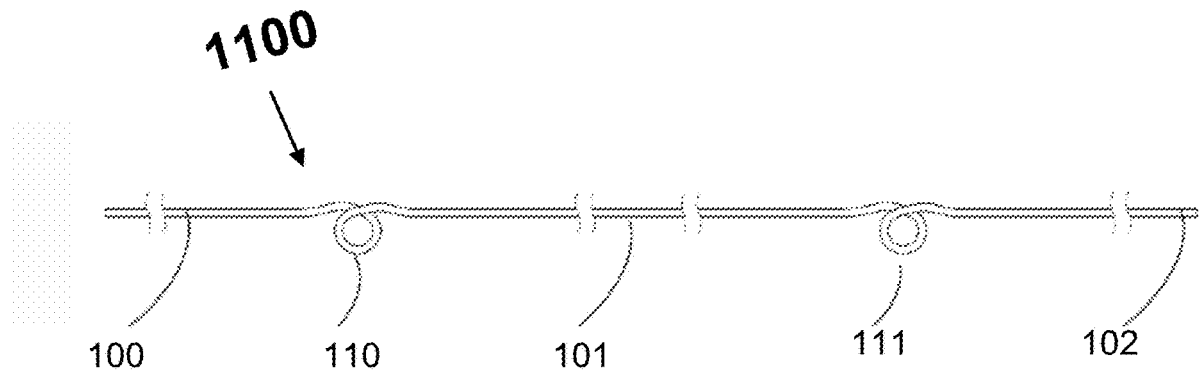
FIG. 3A to 3D are illustrating examples of assembly embolic protection devices for transvascular delivery.

FIG. 3A is illustrating one way of manufacturing the support frame of the protection device. FIG. 3A illustrates here a wire 1100, such as a spring wire, that has been heat treated to form the different sections of the support frame. 110 and 111 are spring sections that will form the distal and proximal spring section when the two ends of the wire are joined. The spring sections are pre-loaded and shaped to be straight; hence they are open springs with an opening larger than the width of the final device. When the two ends of the wire are joined, the straight sections 100 and 102 will provide one straight central section, while the straight section 101 will provide the second straight central section. In some examples, the straight sections are heat treated to be straight. Alternatively, in some examples, the straight sections are not heat treated.

Figure 3B:
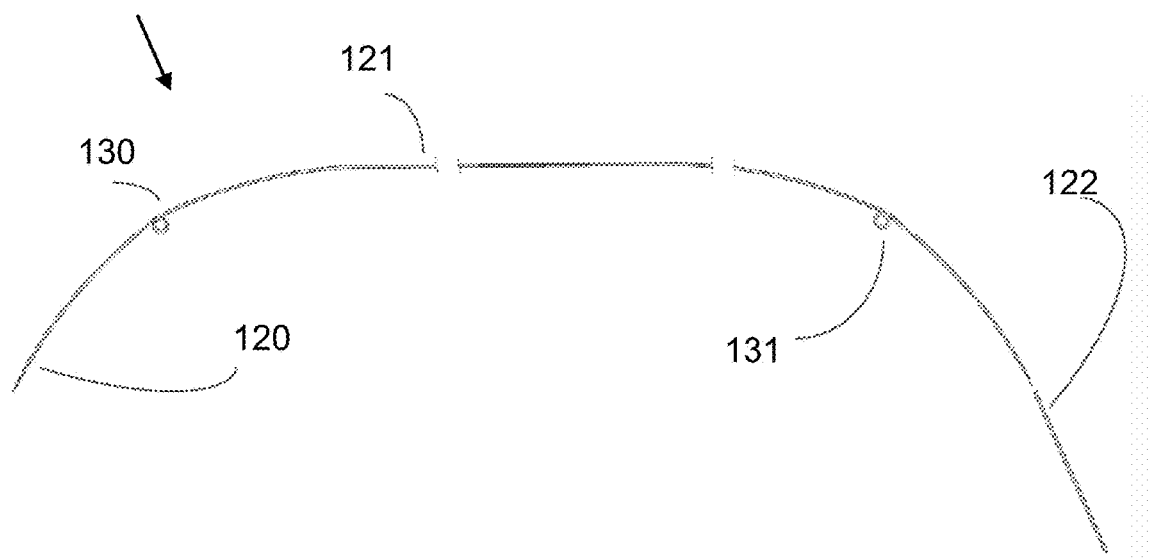

FIG. 3B is illustrating an alternative way of manufacturing the support frame of the protection device from a wire 1101, such as a spring wire. In this example the wire 1101 has been heat treated to form the different sections of the support frame. 130 and 131 are spring sections that will form the distal and proximal spring section when the two ends of the wire are joined. The spring sections are pre-loaded and shaped to be curved. The openings of the spring sections are here larger than the width of the final device. When the two ends of the wire are joined, the straight sections 120 and 122 will provide one straight central section, while the straight section 121 will provide the second straight central section. In some examples, the straight sections are heat treated to be straight. Alternatively, in some examples, the straight sections are not heat treated.

Figure 3C:
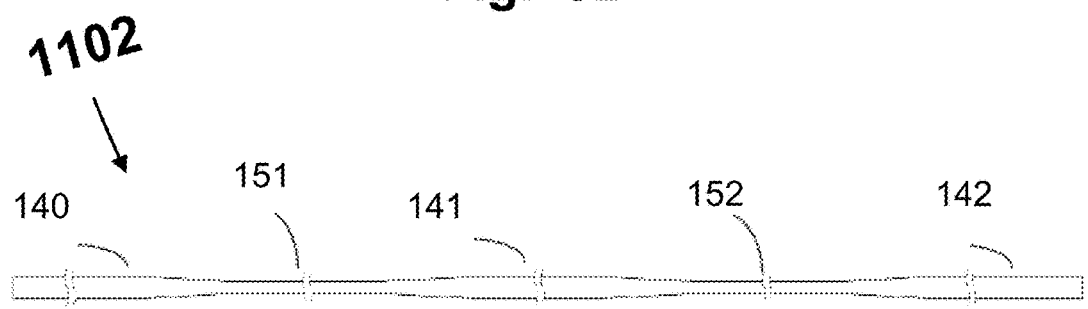

FIG. 3C is illustrating an alternative way of manufacturing the support frame of the protection device from a wire 1102. The wire 1102 is a grinded wire having more than one tapered section. In illustration there are three thicker sections and two thinner sections 151, 152. The thinner sections may be forms into two straight central sections while the three thicker sections 140, 141, 142 will form two spring sections when the two ends of the wire 1102 are joined.

Additionally, and/or alternatively, in some examples, the thicker sections 140, 141, 142 that will form the two spring sections may have spring elements. In some examples the thicker sections 140, 141, 142 that will form the two spring sections may be curved as in FIG. 3B.

Additionally, and/or alternatively, in some examples, the wire 1102 may include thicker tapered sections, similar as the sections used for the spring sections, to be used for the straight central sections. Between the thicker tapered sections there will be thinner sections forming joints or transitions between the different spring sections and the straight central sections.

A wire 1102 with tapered thicker sections with thinner sections between may allow one wire 1102 to be configured to result in a support frame with different forces at different segments.

Further, instead of having one single grinded wire 1102 as in FIG. 3C each section may be formed from a single grinded wire with only one tapered thicker section and thinner segments at the sides. These sections may then be joined as illustrated in FIG. 3D.

Figure 3D:
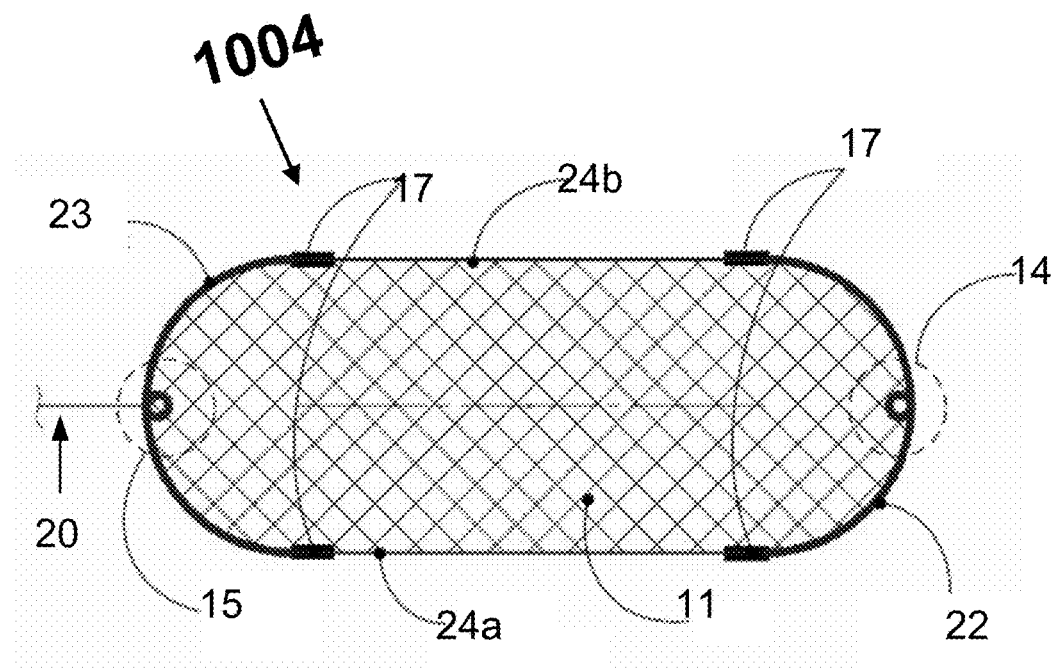

FIG. 3D is illustrating an embolic protection device 1004 wherein the support frame is made from 4 separate segments, functioning as engines. The segments include, a distal spring section 22, a proximal spring section 23, and two central straight sections 24a, 24b. A filter member 11 is attached to the support frame.

Each of the distal and proximal spring sections 22, 23 may have a spring element 14, 15. The spring sections 22, 23 are engines being pre-shaped open springs, which in some examples has a shallow U-shape. In some other examples the spring sections are straight before the support frame is assembled. The spring sections 22, 23 may have a radius wider than the embolic protection device. Different radius of the opening may provide different forces.

In between the spring sections 22, 23 are straight central segments 24a, 24b arranged. In some examples, the straight central segments 24a, 24b are not heat treated while the spring sections 22, 23 are.

In some examples, the proximal 23 and distal 22 spring section may differ, for example by providing different amount of forces. The distal spring section 22 may provide improved apposition with aortic arch walls which may improve fixation of the device 1004 and the sealing between the device and the aortic wall, which may reduce paraframe leakage. The proximal spring section 23 covers the landing zone of the embolic protection device. The landing zone is the area every guidewire will hit the aortic arch inner vessel wall when femorally introduced into the aortic arch. Hence a better apposition between the embolic protection device and the walls of the aortic arch is obtained as an advantage.

Due to the positioning of the proximal end, a strong force is not as important as at the distal end of the device. The different forces may be provided by making the distal spring section 22 thicker than the proximal spring section 23. The spring element 14 at the distal section 22 may also be configured to provide a stronger force than the spring element 15 at the proximal spring section 23.

In some examples only one of the spring sections 22, 23 includes a spring element 14, 15. The spring element 14, 15 may also be used to improve the crimping of the device. Further, having the proximal spring section 23 being made of a thinner material than the distal spring section 22, may also improve the crimping of the device as the force will be weaker at the proximal section 23.

FIG. 4 is illustrating a collapsible embolic protection device 1005 having a filter element 11 may extend outside the support fame 10, and thereby create a collar or rim 25. The collar or rim 25 may improve apposition with the vessel wall rough texture. Peripheral sealing may thus be improved, in particular as pulsatile flow presses the collar or rim against the inner aortic arch vessel tissue. In some examples, the collar or rim may be made from a different material than the filter member 11, such as PTFE or a fabric, e.g. Dacron. The collar may have in addition or alternatively a non-filtering configuration, such as a sheet of material without filter, e.g. a film.

Figure 5:
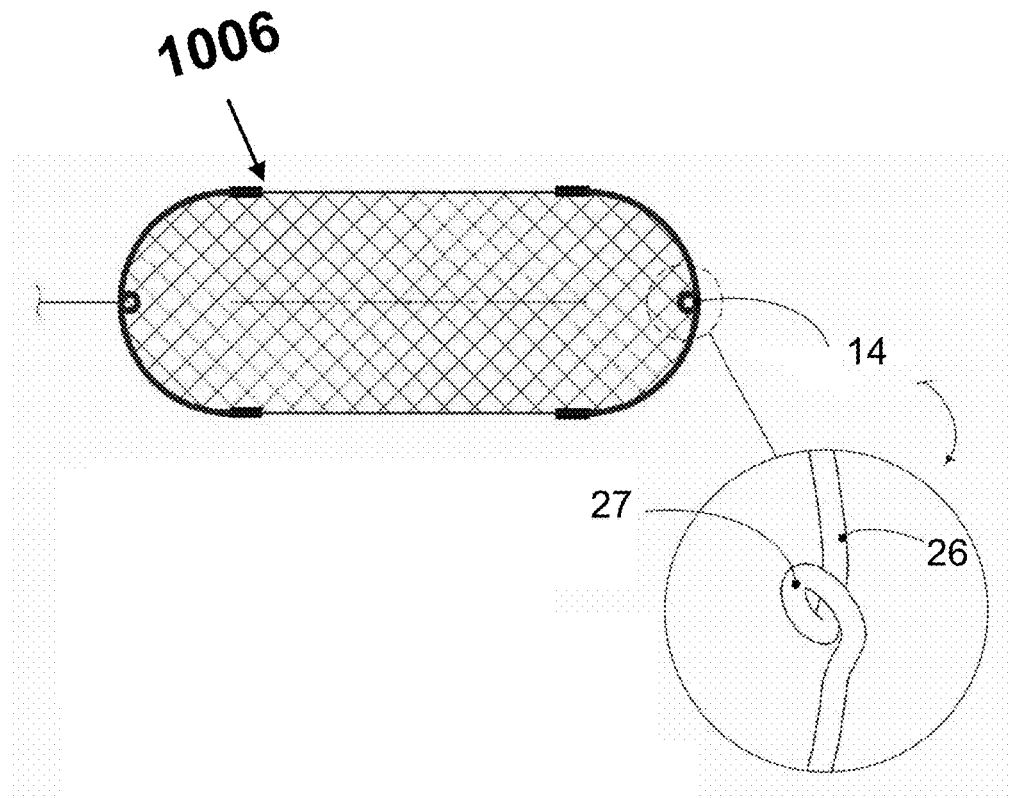
FIGS. 5 and 6 are illustrating additional examples of spring segments for improving the spring effect.
Figure 6:
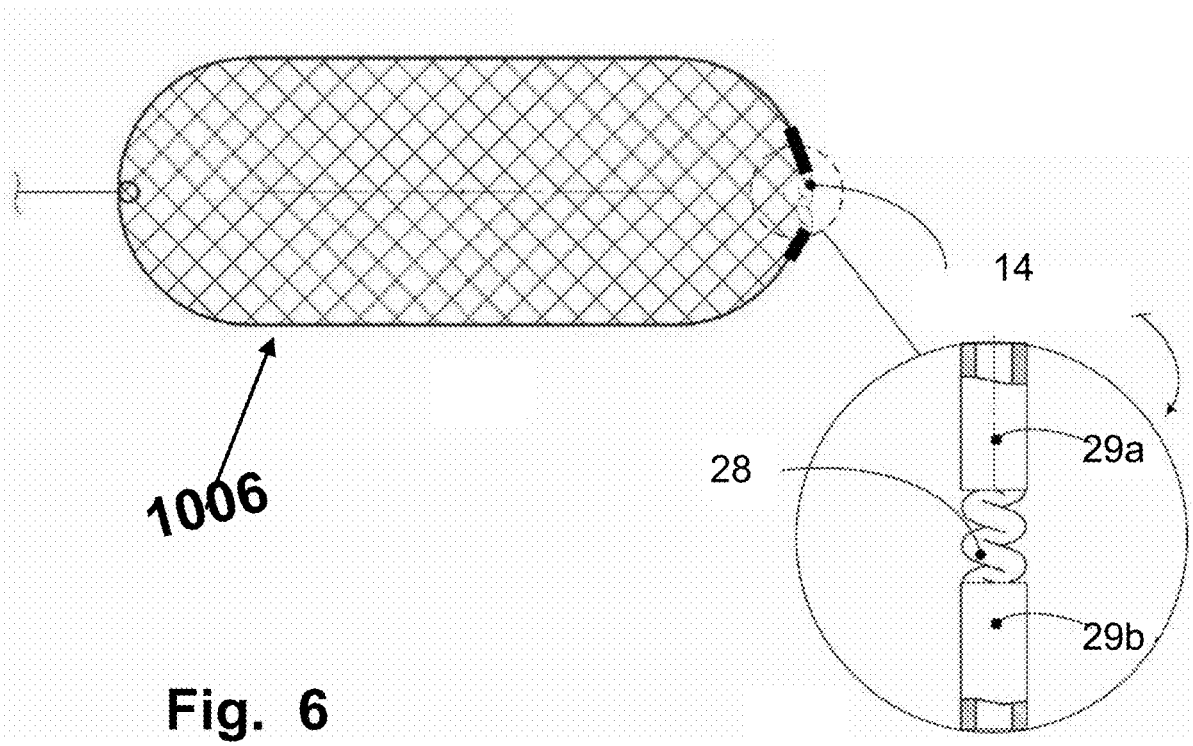

FIGS. 5 and 6 are illustrating two examples of spring elements 14 at the distal spring section of the device 1006. The same type of spring element may be used at the proximal spring section.

In some examples, different spring elements are used at the distal and the proximal end.

Those skilled in the art will readily appreciate that other spring elements than those illustrated here may be used to achieve the same effect of improving the force of the spring section against the wall of the aortic arch.

FIG. 5 is illustrating a spring element 14 being a loop 27 formed from the material 26 used to shape the distal spring section, here it is illustrated as a wire, such as a spring wire.

FIG. 6 is illustrating a spring element 14 being a spring 28 attached to a gap in the distal spring section by clamps 29a, 29b. Cross section of the frame may in this manner be held at that of the frame by having an intermediate spring, such as crimped in FIG. 6.

Figure 7A:
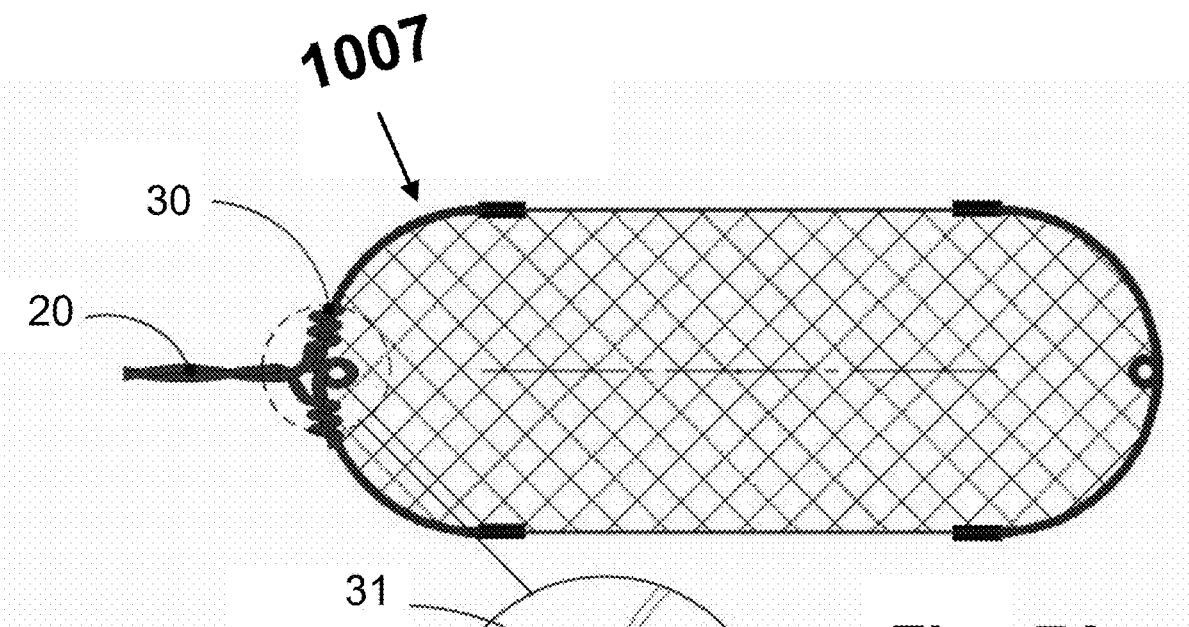
FIGS. 7A and 7B are illustrating examples of connecting the device to a delivery unit.
Figure 7B:
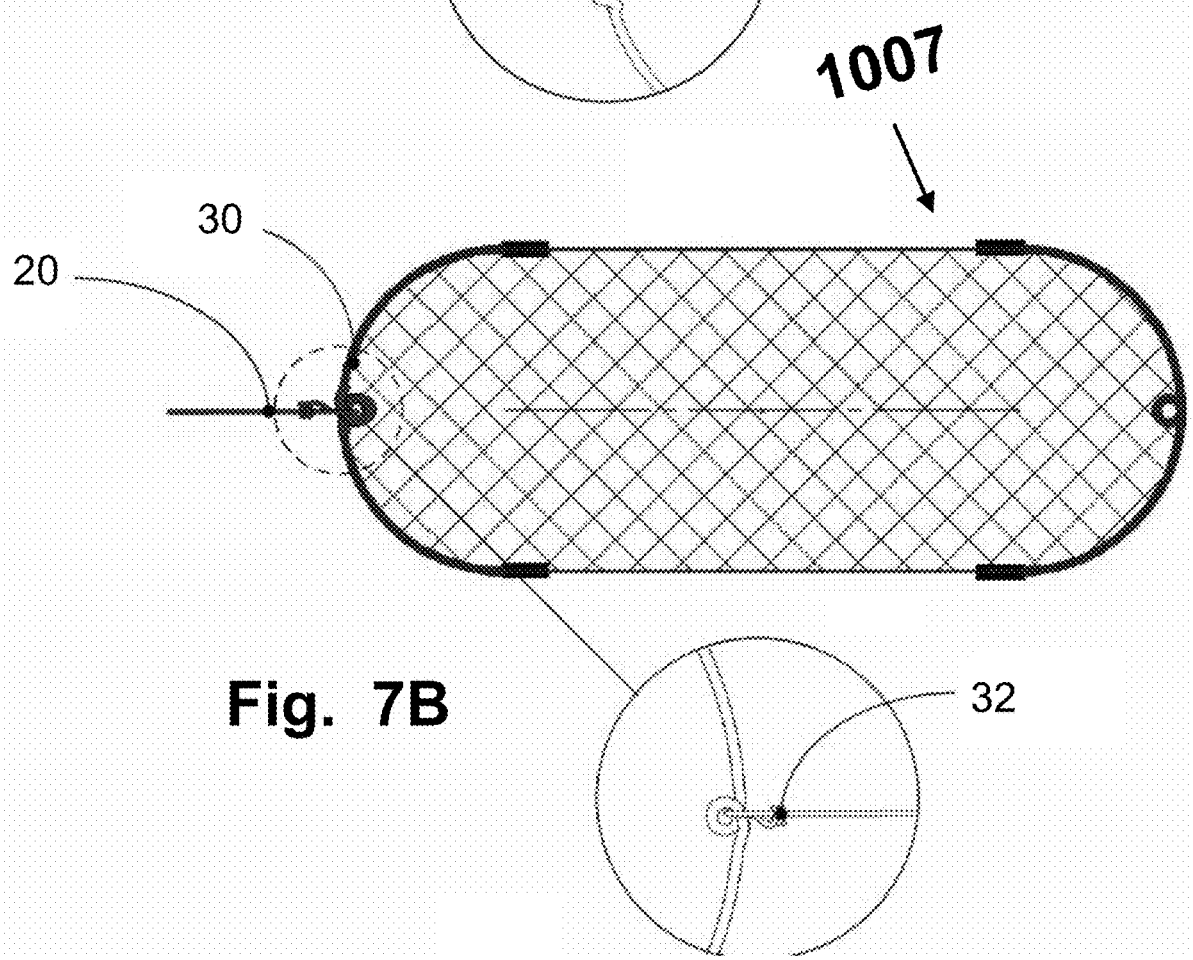

FIGS. 7A and 7B are illustrating two examples of connecting the device 1007 to a connector mechanism 20, such as a wire, rod or tube, for example, a tether, a delivery wire, or a push wire etc.

FIG. 7A is illustrating the connection point 30 is arranged at the proximal spring section of the support frame. The connector mechanism 20 is here a twisted wire 31 twisted around the support frame. In some examples, the connector mechanism 20 is locked at a pre-set angle. In some other examples, the connector mechanism 20 is made so that the protection device may pivot in an axial direction at the connection point. In some examples, the device is prevented to pivot in a radial direction. In some examples, the connection is made to fixate the protection device in a pre-defined angle.

FIG. 7B is illustrating the connection point 30 is arranged at the proximal spring section of the support frame. The connector mechanism 20 is here a single wire 32 connected to a loop at the proximal spring section. In some other examples, the connector mechanism 20 is made so that the protection device may pivot in an axial direction at the connection point. In some examples, the device is prevented to pivot in a radial direction. In some examples, the connection is made to fixate the protection device in a predefined angle.

FIGS. 8A to 8D are illustrating an example of embolic protection device 1008 being arranged over a wire, ribbon, or tube, such as a leading tube or shaft tube, 35. The wire, ribbon, or tube, such as a leading tube or shaft tube, 35 is used for delivering the embolic protection device 1008. The wire, ribbon, or tube, may be made from either plastic commonly used for catheters or metal, such as a shape memory alloy, such as Nitinol.

Figure 8A:
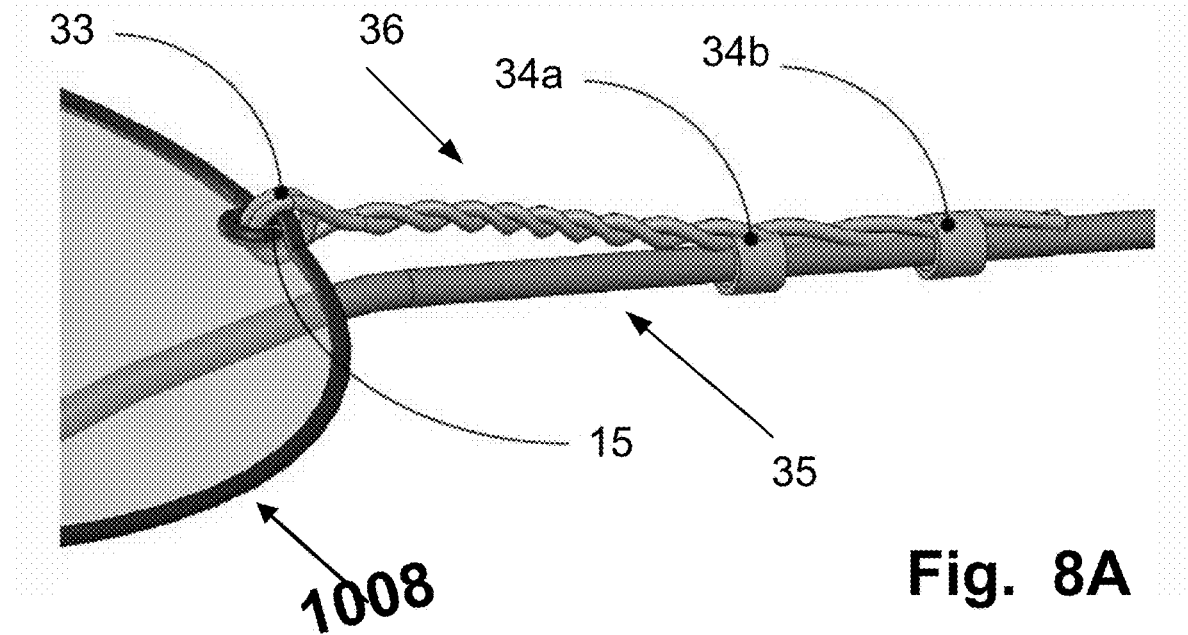
FIGS. 8A to 8D are illustrating an example of an embolic protection device connected to a delivery system including a wire or tube.

In FIG. 8A a twisted wire 36 is used as a connector mechanism. The twisted wire 36 is shaped into a loop 33 at the distal end being connected to the spring element 15, which here also function as a connector point. The twisted wire 36, is attached to the wire, ribbon or tube 35 using at least tone ring 34a, 34b.

Figure 8B:
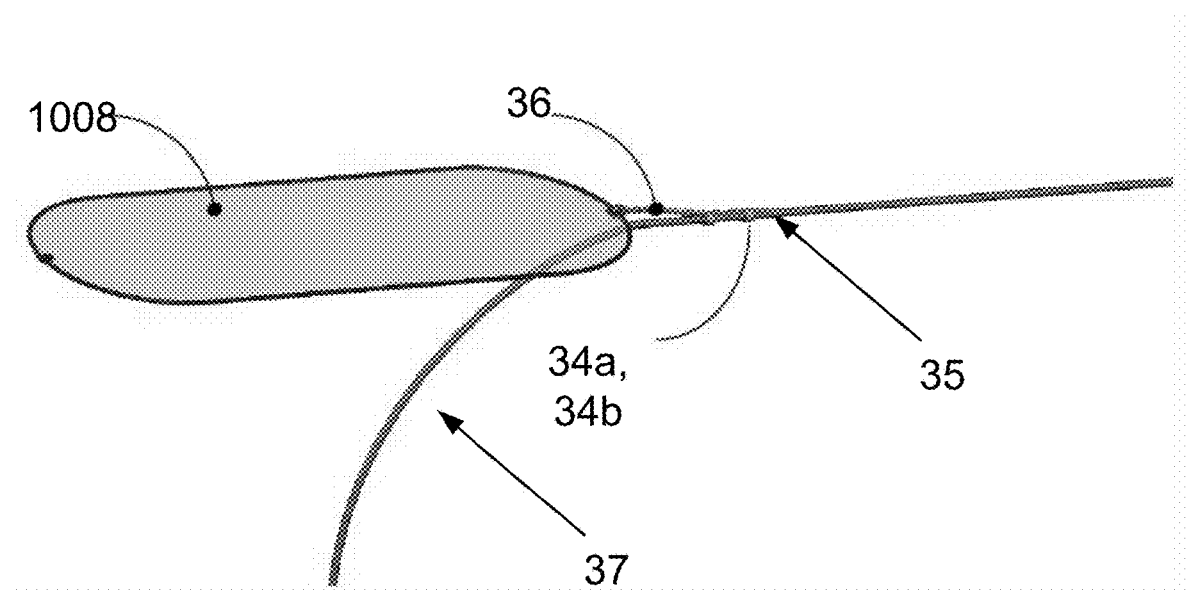
Figure 8C:
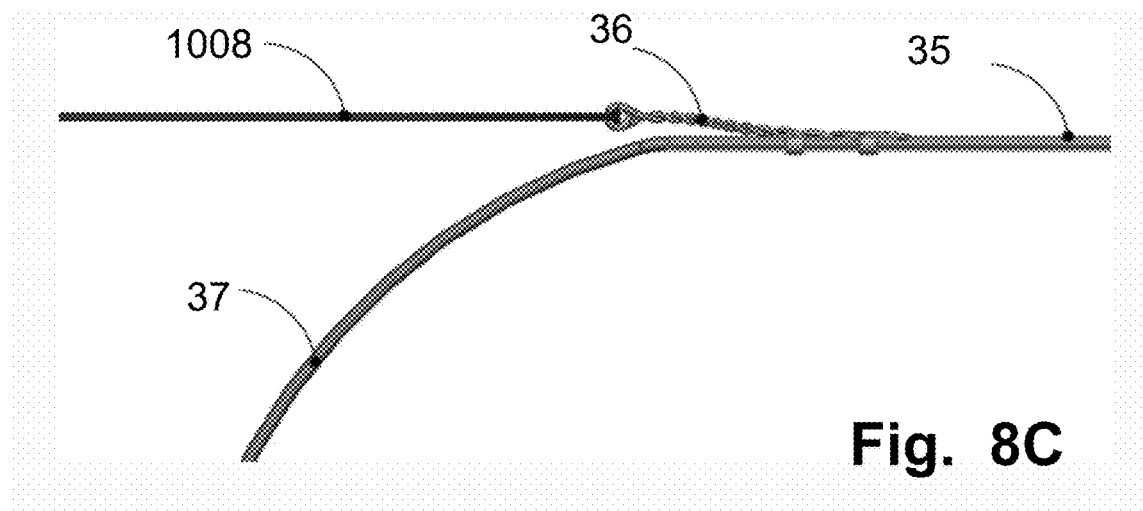
Figure 8D:
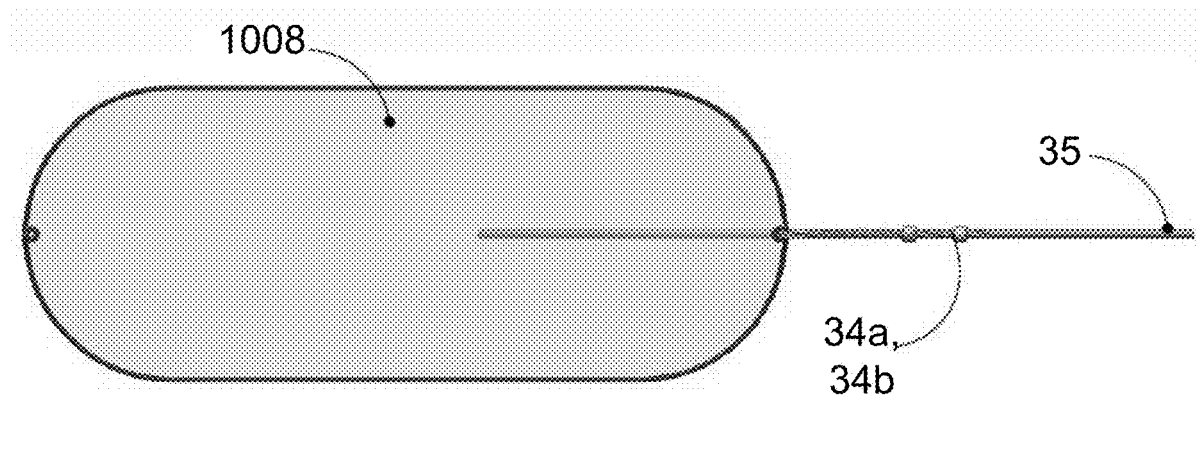

The wire 36 may be made from a shape memory alloy, such as Nitinol. The wire 36 may be a wire twisted and heat treated on a jig and thereby formed into flexible connector mechanism. The wire 36 may place the embolic protection device 1008 perpendicular to the wire tube bend 37, as seen in FIG. 8B to 8D. In some examples, the device may pivot at the connection point in an axial direction, for example during deployment in the aortic arch. In some examples, the device is prevented to pivot in a radial direction. The over the wire arrangement helps to support the filter member by pushing or forcing the filter member or support frame upwards by a dedicated bent tube or wire 37. The arrangement also helps to keep the embolic protection device 1008 in place by the same upward push or force by the bent tube or wire 37. The arrangement may also improve the positioning of the embolic protection device 1008 in the aortic arch.

Figure 9A:
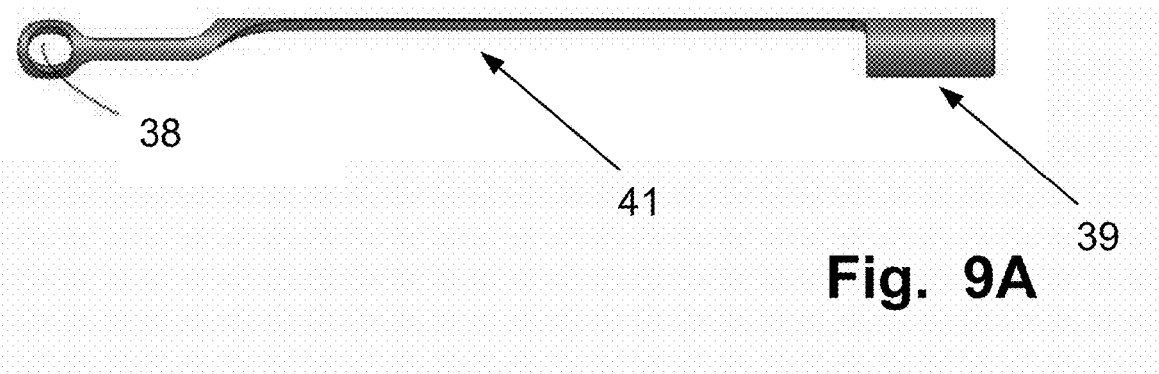
FIGS. 9A to 9C are illustrating a further example of connecting the device to a delivery unit.
Figure 9B:
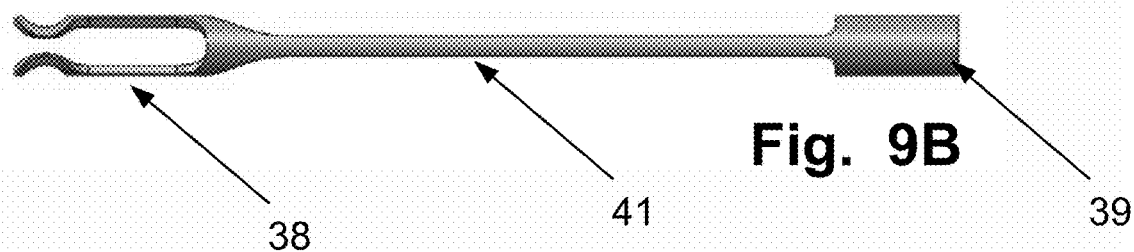
Figure 9C:
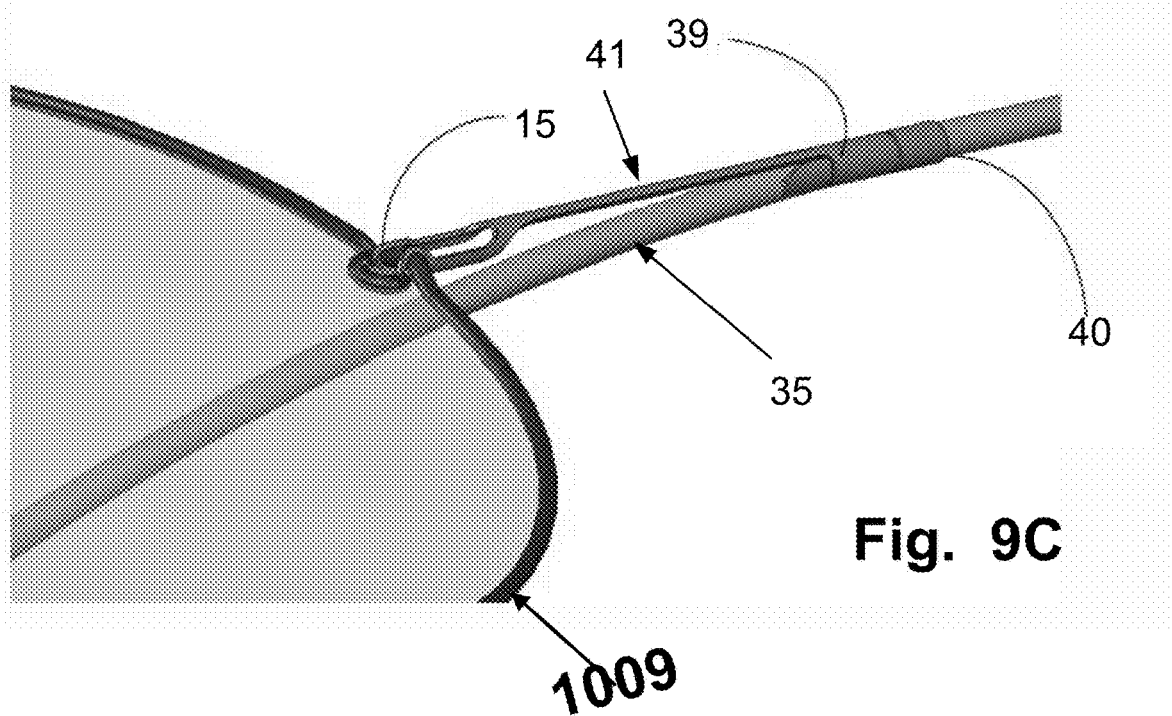

FIGS. 9A to 9C are illustrating a further example of embolic protection device 1009 being connected to be arranged over a wire or tube 35 used for delivering the embolic protection device 1009.

In the illustrated example, the connection mechanism 41 is made from a laser cut tube. The distal end of the connection mechanism 41 is cut as a loop or hole 38 used for attaching the connection mechanism 41 to the embolic protection device 1009. The connection mechanism 41 may be attached either to the frame or to a spring section 15 shaped as a loop. The distal end of the connection mechanism 41 may be shaped to have two branches as seen in FIG. 9B, each branch having a loop or hole.

The proximal end of the connection mechanism 41 is formed as a connector 39 and used to connect the connection mechanism 41 to the wire or tube 35. To fixate the connection mechanism 41 to the wire or tube 35 a stopper 40 is used. An example of a stopper 40 is illustrated in FIGS. 11A and 11B.

In some examples, the stopper 40 is welded to wire or tube 35 to better fixate the connection mechanism 41 at the needed position.

In some examples, the device may pivot at the connection point in an axial direction, for example during deployment in the aortic arch. In some examples, the device is prevented to pivot in a radial direction.

Figure 10A:
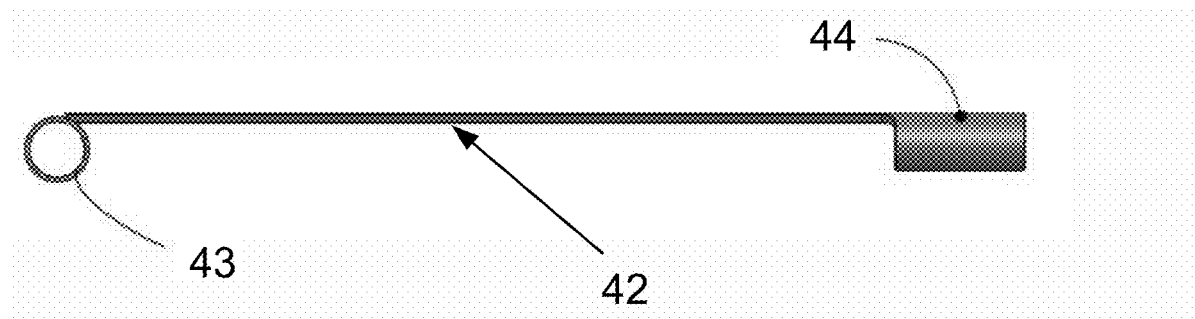
FIGS. 10A to 10C are illustrating a further example of connecting the device to a delivery unit.
Figure 10B:
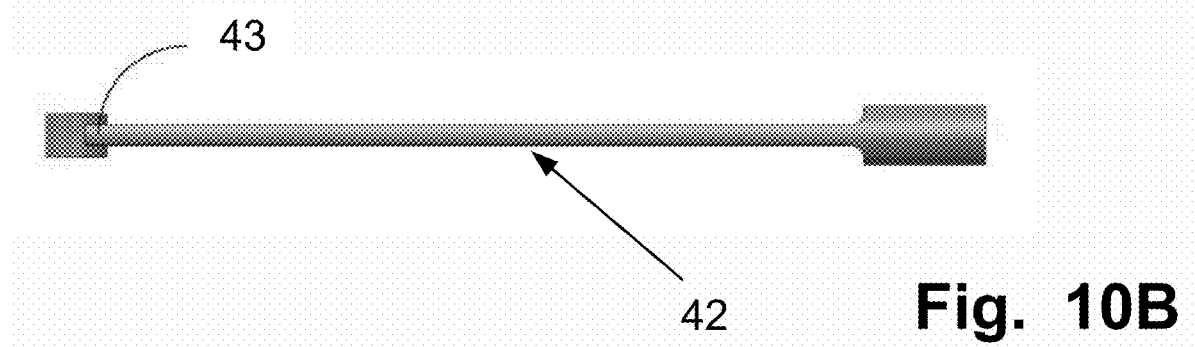
Figure 10C:
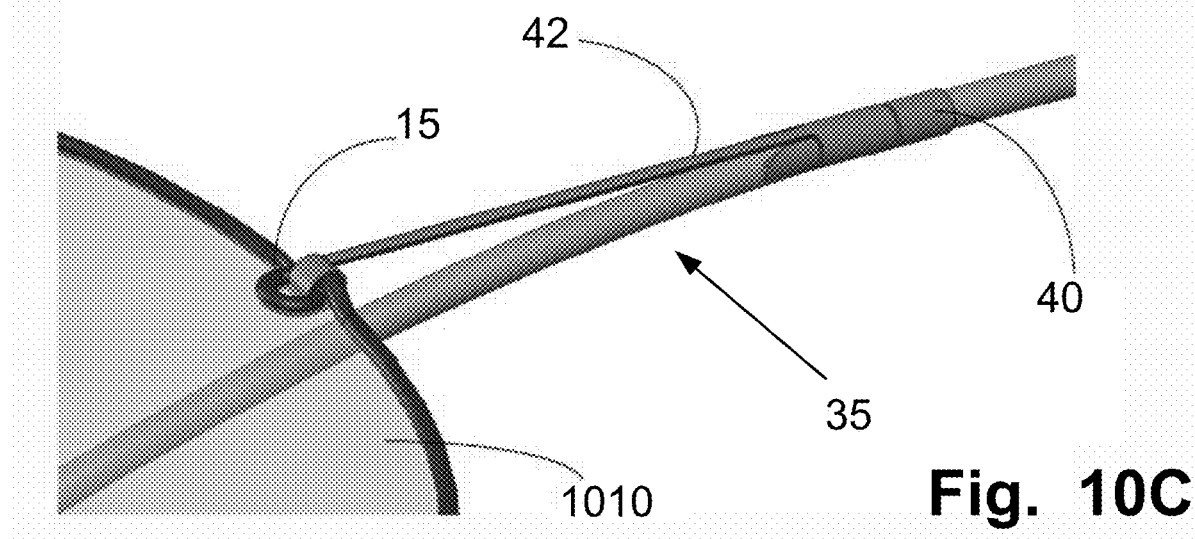

FIGS. 10A to 10C are illustrating a further example of embolic protection device 1010 connected to be arranged over a wire or tube 35 used for delivering the embolic protection device 1010.

In the illustrated example, the connection mechanism 42 is made from a laser cut tube. The distal end of the connection mechanism 42 has a ring 43 welded to it. The ring 43 is used for attaching the connection mechanism 42 to the embolic protection device 1010. The connection mechanism 42 may be attached either to the frame or to a spring section 15 shaped as a loop.

The proximal end of the connection mechanism 42 is formed as a connector 44 and used to connect the connection mechanism 42 to the wire or tube 35. To fixate the connection mechanism 42 to the wire or tube 35 a stopper 40 is used. An example of a stopper 40 is illustrated in FIGS. 11A and 11B.

In some examples, the stopper 40 is welded to wire or tube 35 to better fixate the connection mechanism 42 at the needed position. In some examples, the device may pivot at the connection point in an axial direction, for example during deployment in the aortic arch. In some examples, the device is prevented to pivot in a radial direction.

Figure 12A:
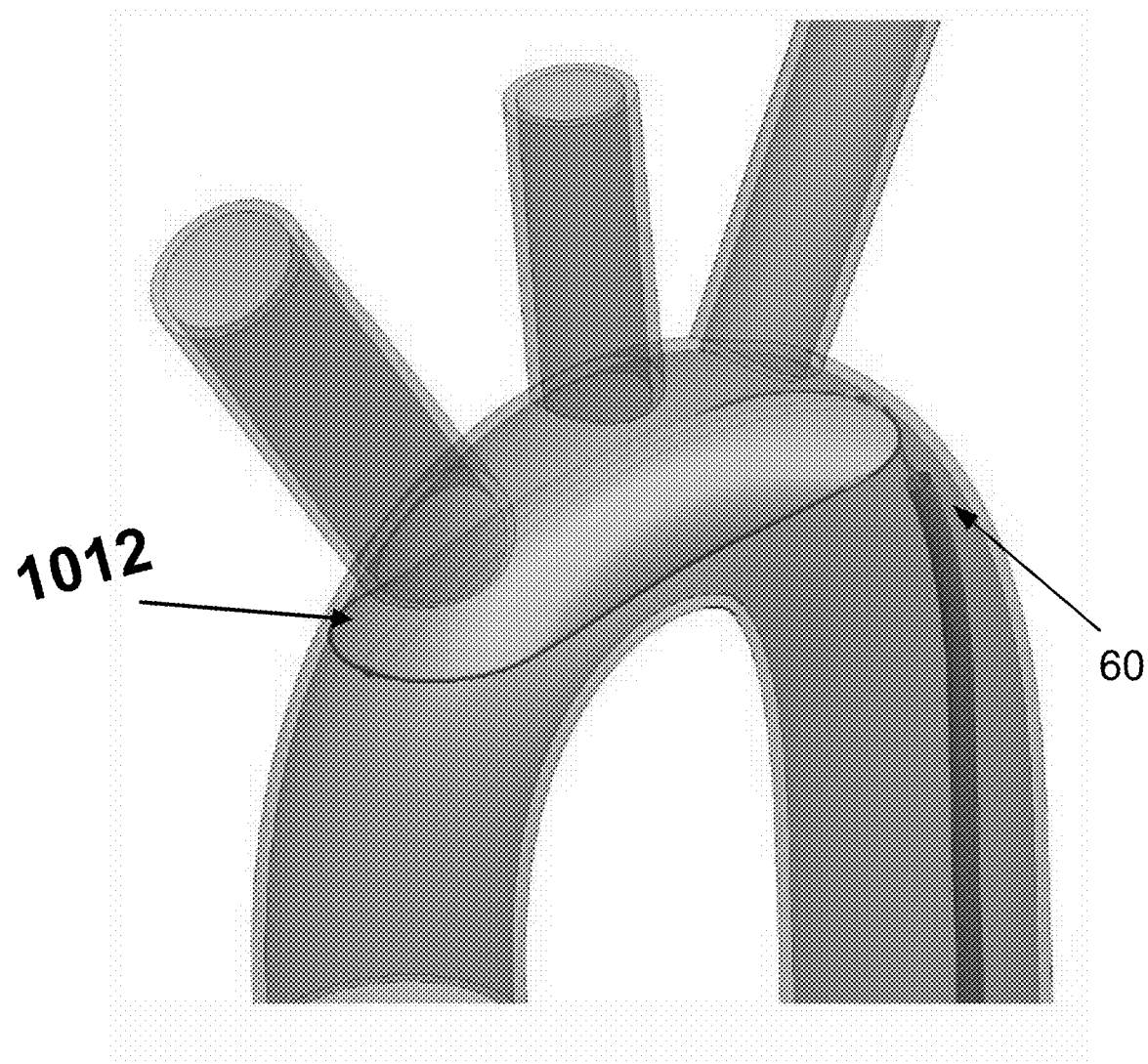
FIG. 12A to 12C are illustrating examples of an embolic protection devices positioned in an aortic arch.

FIG. 12A is illustrating a protection device 1012 arranged in the aortic arch. The device is delivered and held by the catheter or sheath 60 during the procedure. In the illustrated example the protection device 1012 covers all three side branches of the aortic arch.

Figure 12B:
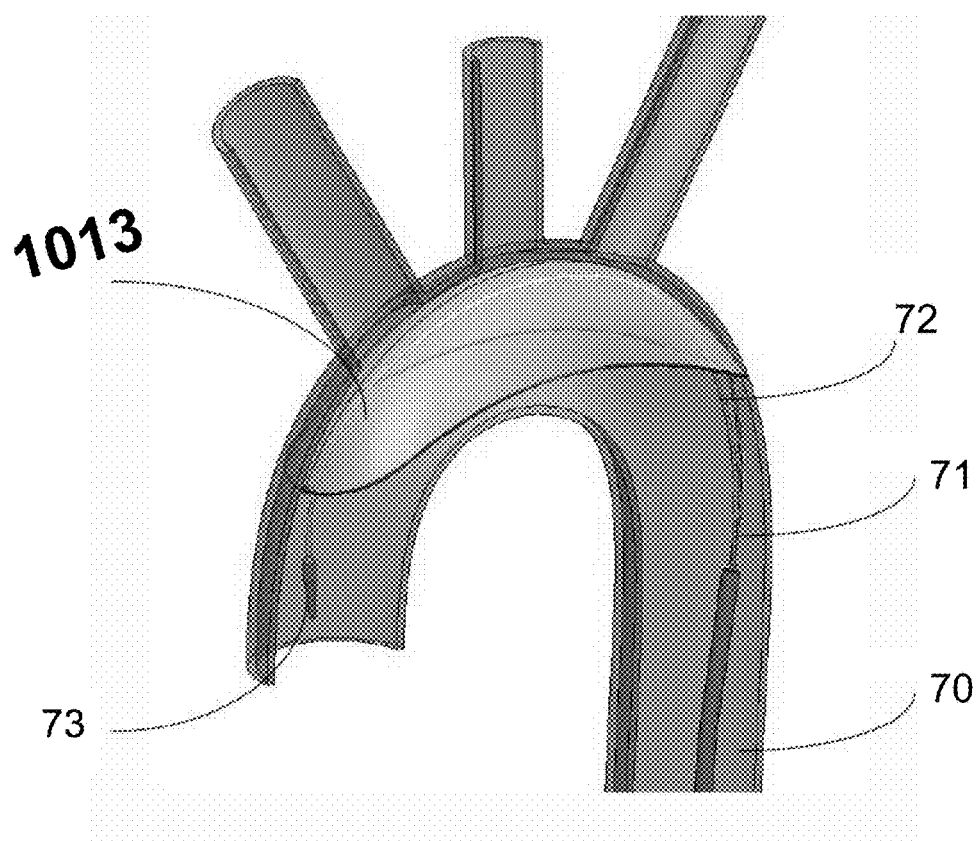

FIGS. 12B and 12B are illustrating a protection device 1013 arranged in the aortic arch. The device is connected to a wire or, ribbon or tube 72 by a connection mechanism 71. The device is delivered by the catheter or sheath 70.

The wire or, ribbon or tube 72 has a dilator tip 73. The dilator tip 73 may be an atraumatic tip.

Figure 12C:
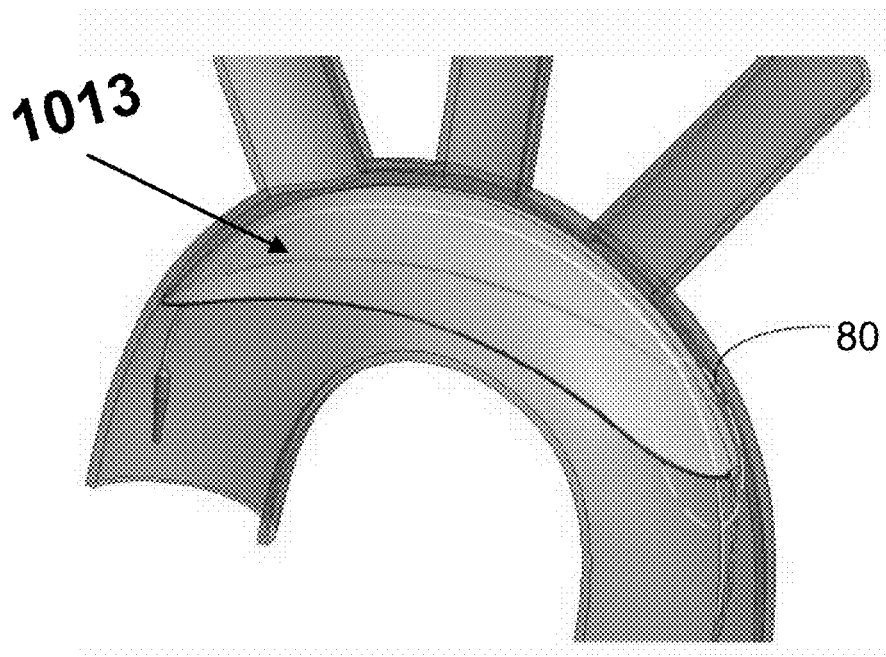

FIGS. 12B and 12B are illustrating are illustrating that the bend of the wire or, ribbon or tube 72 helps to support the filter member by pushing or forcing the filter member or support frame upwards. The arrangement also helps to keep the embolic protection device 1013 in place using the same upward push or force by the bent tube or wire 72. FIG. 12C is illustrating the landing zone 80.

In some examples, the wire, ribbon or tube 72 may be pre-bend. The pre-bend may be calculated based on the curvature of the anatomy of the aortic arch. An advantage of this is that it may prevent the embolic protection device from flipping during insertion or during a procedure when the embolic protection device is arranged in the aortic arch.

FIGS. 13A to 13E are illustrating a method for making a dome shaped filter element 1011. The dome-shaped filter member 1011 may be made from a woven mesh 50 made from, for example a polymer, such as Polyetereterketon (PEEK). The dome-shaped filter member 1011 may be formed by cutting openings or wedges 51a to 51d into the mesh material 50, see e.g. four wedges in FIG. 13A.

Figure 13A:
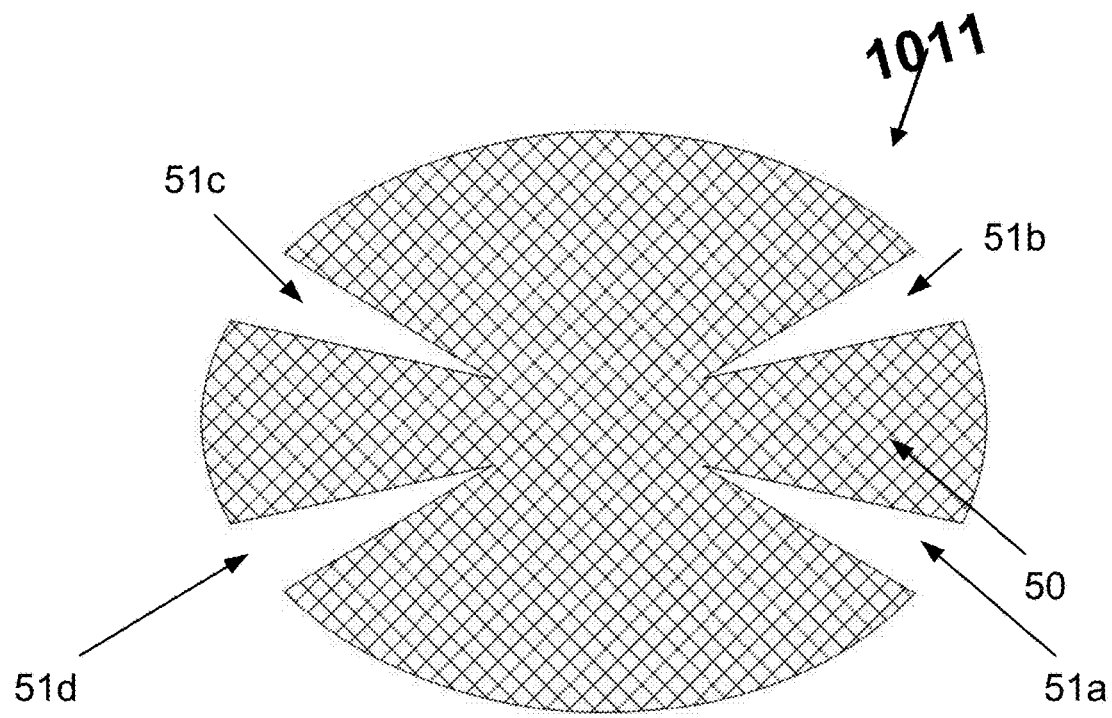
FIGS. 13A to 13E are illustrating an example of a dome-shaped filter member.
Figure 13B:
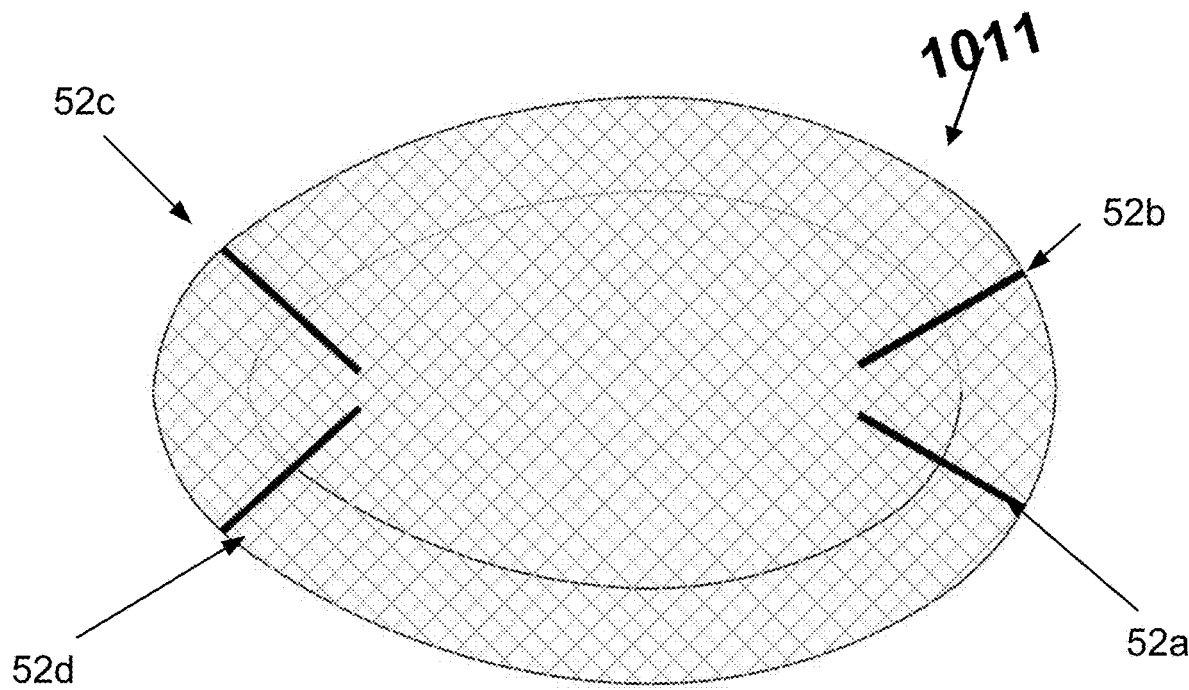

The dome-shape is then shaped by attaching the edges of each openings or wedges 51a to 51d. By gluing, heat welding, ultrasonic welding etc., 4 seams 52a to 52d will be obtained, as illustrated in FIG. 13B.

Figure 13C:
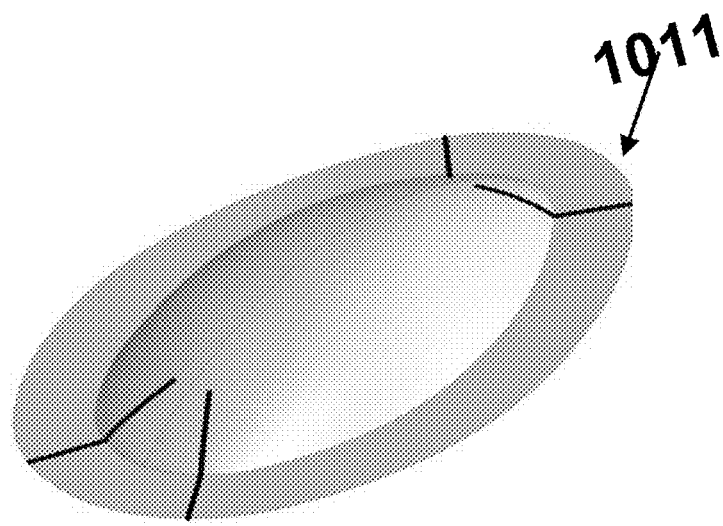
Figure 13D:
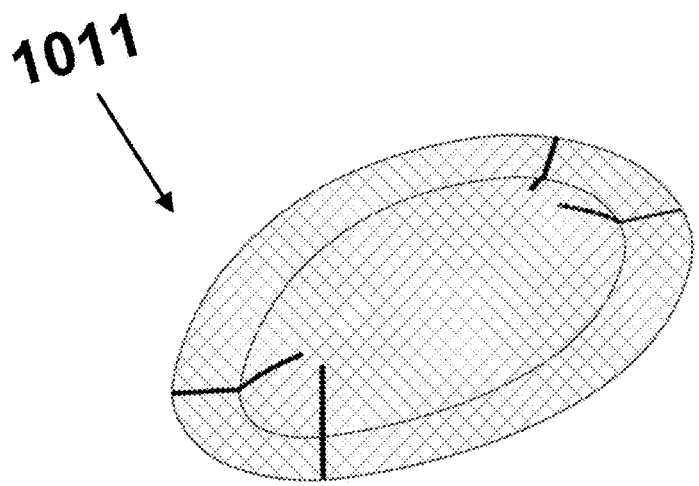
Figure 13E:
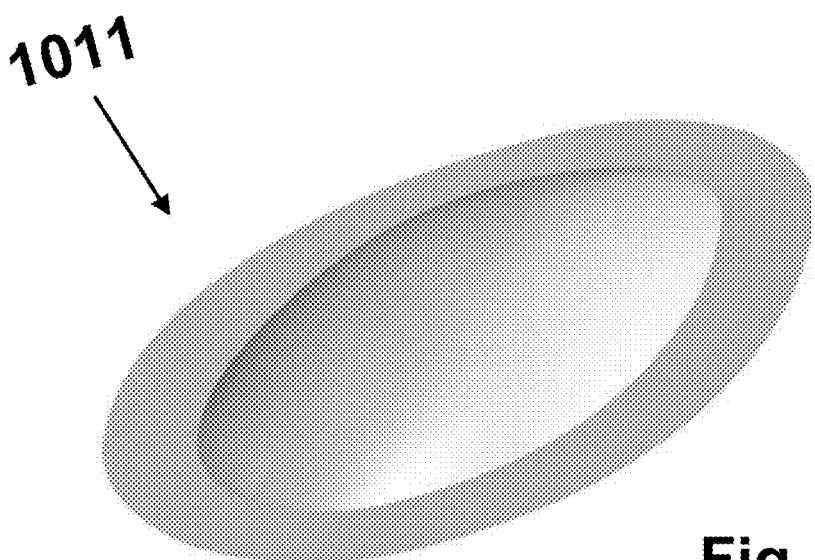

The heat forming allows the dome-shaped filter member 1011 to obtain a three-dimensional shape from a flat 2d mesh layer. The three-dimensional dome-shape is illustrated in FIGS. 13C to 13E. In some examples, the three-dimensional dome-shape is seamless. In some examples the three-dimensional dome-shape is thus formed without creases as illustrated in FIGS. 13C to 13E.

In some examples, the three-dimensional structure, such as the dome-shape, may appear almost flat when attached to the frame and the frame is not constrained. When the frame is constrained, such as by the walls of the aortic arch, mesh will go back to the formed three-dimensional structure.

FIGS. 14A to 14C are illustrating an example of stickers or patches 1014, 1015 that may be arranged at a distal and/or a proximal end of the embolic protection device 1016. The sticker or patch 1014, 1015 may preferably be made from an elastic material, such as polyurethane. The sticker or patch 1014, 1015 may be either solid or porous, such as made as a mesh. The sticker or patch 1014, 1015 may be shaped like a square or rhombus, such as having a diamond-like shape.

In FIGS. 14A and 14B the distal patch 1015 and the proximal patch 1014, are dimensioned as rhombuses but with a cut out in the middle, creating a waist section 102. The waist section 102, 104 makes it easier to attach the sticker or patch 1014, 1015 to the embolic protection device 1016, since there will be less material folded over or stretched around the frame 103 and thereby attached thereto. Because of the curvature of the frame, the patch or sticker 1014, 1015 may not be smoothly folded or stretched over and attached to the frame 103, which may cause wrinkles in the sticker or patch 1014, 1015 at the frame 103. This may be prevented by having a waist section 102, 104 as illustrated in FIGS. 14A and 14B.

Alternatively, in some examples, the stickers or patches 1014, 1015 may be triangular. When triangular, the sticker or patch 1014, 1015 is not folded around the frame 103, instead they are only attached to one side of the filter of the embolic protection device 1016.

The proximal patch 1014, illustrated in FIG. 14A, has a cut-out in the middle 104, which allows a connection mechanism 101 to be used to connect the embolic protection device 1016 to a wire, ribbon or tube, as previously described herein.

The stickers or patch 1014, 1015 is adhered to the filter mesh of the embolic protection device 1016. The sticker or patch 1014, 1015 may adhered to the embolic protection device using glue or an adhesive layer. The sticker or patch 1014, 1015 may also be attached using heat. In some examples both glue or an adhesive layer, is used with heat to attach the sticker or patch 1014, 1015 to the embolic protection device 1016.

The sticker or patch 1014, 1015, may provide more strength to the embolic protection device 1016 when crimped. The sticker or patch covers part of the structure from blood where otherwise thrombus may be formed.

The sticker or patch 1014, 1015, may also be used to attach the mesh of the embolic protection device 1016 to the frame 103 at the distal and/or proximal end. This may have an advantage when the distal and/or proximal spring section has a spring element, such as a loop or helix. By avoid gluing the mesh to the spring element and instead using the sticker or patch 1014, 1015 to attach the distal end proximal end of the mesh to the frame 103 at these point, the spring elements may be more effective, because they are not restricted by the mesh or by glue. This may be archived by not having any adhesive means, such as glue at the waist section 102, 104 which is stretched over the frame and the spring element.

Figure 15A:
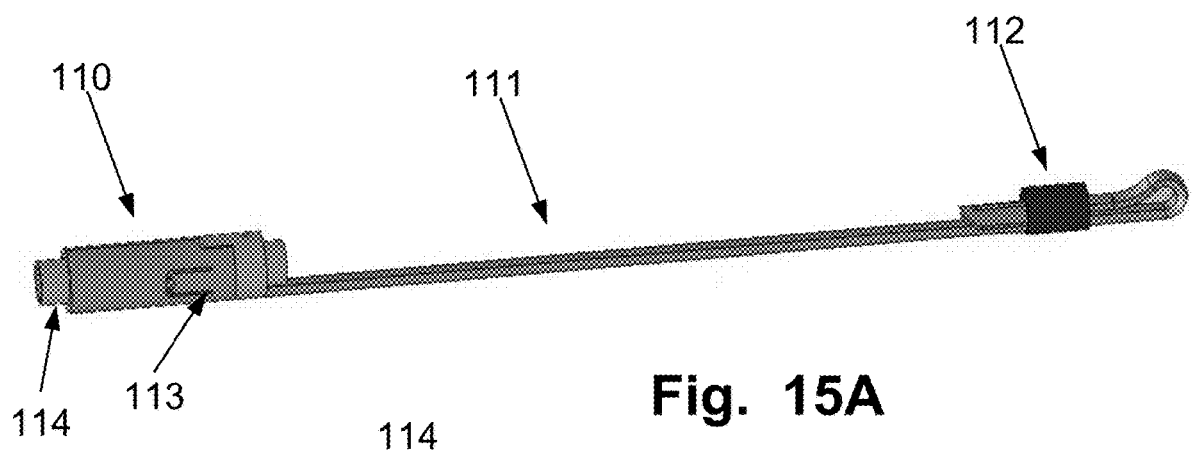
FIGS. 15A to 15C are illustrating a further example of connecting the device to a delivery unit.
Figure 15B:
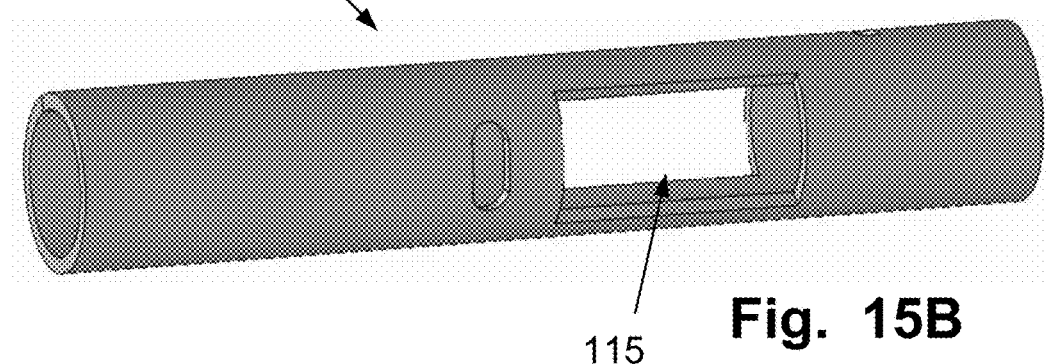
Figure 15C:
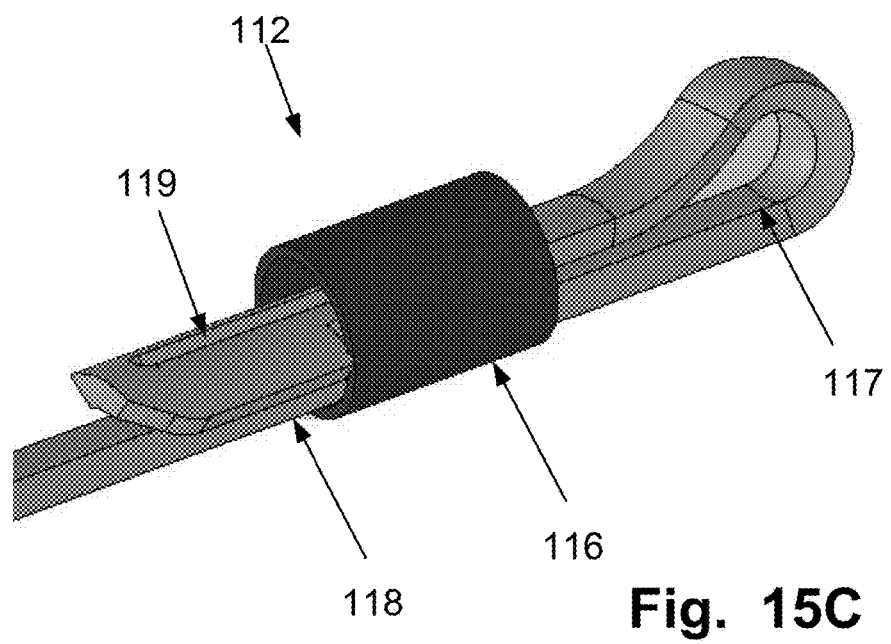

FIGS. 15A to 15C are illustrating a further example of connecting the device to a delivery unit. The example illustrated in FIG. 15A to 15C is similar to the examples described in relation to FIGS. 8 to 11. The connector mechanism 111 illustrated in FIG. 15A has a distal end section 112 and a proximal end section 110. The distal end section is designed to be connected to the frame of an embolic protection device and the proximal end section is designed to be connected to a wire, tube or ribbon which goes under the embolic protection device, see for example FIGS. 8B and 21B and 12C. The proximal end section 110 of the connector mechanism 111 forms a hollow cylindrical body which may be slide over the wire, tube or ribbon 114 (in the illustrations only a small portion of the wire, tube or ribbon is shown) until it is securely locked.

The locking may be made by a first locking member 113 of the proximal end section of the connector mechanism 111 engaging with a second locking member 115 of the wire, tube or ribbon. The first locking member 113 may be a letch which is angled into the hollow cylindrical body and engages with a hole or window 115 of the wire. The hole or window may have the same width as the letch, preventing rotation of the connector mechanism 111 around the wire, tube or ribbon after the letch has engaged with the hole or window.

Alternatively, the second locking element 115 of the wire, tube or ribbon may be a letch which is angled outwards so it may engage with a first locking element 113 of the proximal end section 110 of the connector mechanism 111, being a hole or window. Again, the hole or window may have the same width as the letch to avoid rotation of the embolic protection device.

The distal end section 112 of the connecting mechanism is formed by a portion of the connector mechanism 111 being folded back over itself providing a gap 118 therebetween in which a frame of an embolic protection device, such as a wire, may be slide. The distal end of the distal end section 112 may have a wider gap 117. The wider gap 117 may be configured to have a similar diameter as the diameter of the frame of the embolic protection device.

This arrangement is allowing the frame to be arranged firmly at the distal end section 112 while still provide pivotability axially but not radially at the joint between the frame and the connector mechanism 111 when applying a force on the embolic protection device.

To lock the frame in the gap 118, 117 and prevent it from slipping out, a locking ring 116 is slipped over the fold backed portion of the distal end section 112. The locking ring 116 is the locked by having a section 119 of the fold backed portion being wider than the hole through the locking ring. The wider section of the fold backed portion will be crimped when the locking ring 116 is slipped over, and will thereafter expand preventing the locking ring 116 form slipping off. To enhance the flexibility of the wider section of the fold backed portion, and thereby allow it to crimp and expand easier, a slit 119 may be arranged at the middle of at least the wider section.

The connection mechanism 111 illustrated in FIG. 15A, is designed to providing stability and flexibility and to allow a certain degree of freedom without rotation, which allows the wire, tube or ribbon to stay in the right position while the embolic protection device is arranged in the intended position.

While several examples of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Also, different method steps than those described above, performing the method by hardware, may be provided within the scope of the disclosure. The different features and steps of the disclosure may be combined in other combinations than those described. The scope of the disclosure is only limited by the appended patent claims.

The invention claimed is:

1. An embolic protection device for transvascular delivery to an aortic arch of a patient, for protection of side branch vessels of said aortic arch from embolic material, said device including:
    a support frame, wherein at least a distal or a proximal portion of said support frame is a spring section configured for providing a radial force between said support frame and a wall of said aortic arch when in an expanded state;
    a filter member attached to said support frame, and configured for preventing said embolic material from passage with a blood flow into said side branch vessels of said aortic arch;
    said filter member having a pre-formed, non-flat, three-dimensional shape; and,
    said support frame being movable between a non-constrained state where said filter member conforms to a substantially flat shape to a constrained state where said filter member returns to said pre-formed, non-flat, heat-set three-dimensional shape.

2. The device of claim 1, wherein said support frame is a complete hoop.

3. The device of claim 1, where said support frame is made from at least four separate sections including a distal and proximal spring section being heat treated, and at least two central sections.

4. The device of claim 1, wherein said support frame includes at least two central sections which are straight.

5. The device of claim 4, wherein said at least distal or proximal spring section is heat treated while said at least two central sections are not heat treated.

6. The device of claim 1, wherein said at least distal or proximal spring section includes at least one spring element configured to increase said force of said spring sections.

7. The device of claim 1, where said pre-formed, non-flat, three-dimensional shape of said filter member is a dome shape.

8. The device of claim 1, wherein said support frame is made from a wire or is laser cut.

9. The device of claim 1, wherein said support frame is thicker at least at said distal section or said proximal section, compared to any other part of said support frame.

10. The device of claim 1, further comprising a transvascular delivery unit which comprises a wire or tube.

11. The device of claim 10, wherein a connection point is arranged at a proximal portion of said filter member or said support frame.

12. The device of claim 10, wherein said wire or tube continues in a longitudinal direction under said support frame and said filter member toward a distal end of said device when arranged in the aortic arch.

13. The device of claim 12, wherein said wire or tube is bent after said connection to said connection point.

14. The device of claim 10, wherein said wire or tube has a dilator tip at a distal end which is atraumatic.

15. The device of claim 6, wherein said at least one spring element is a loop arranged at about a center of each of said at least distal or proximal spring section.

16. The device of claim 15, wherein each of said at least distal or proximal spring section is arranged at a proximal or at a distal end of said support frame.

* * * * *